United States Patent [19]

Babin et al.

[11] Patent Number: 5,360,938
[45] Date of Patent: Nov. 1, 1994

[54] ASYMMETRIC SYNTHESES

[75] Inventors: James E. Babin, Hurricane; Gregory T. Whiteker, Charleston, both of W. Va.

[73] Assignee: Union Carbide Chemicals & Plastics Technology Corporation, Danbury, Conn.

[21] Appl. No.: 911,518

[22] Filed: Jul. 16, 1992

Related U.S. Application Data

[63] Continuation-in-part of Ser. No. 748,112, Aug. 21, 1991, and Ser. No. 748,111, Aug. 21, 1991, abandoned.

[51] Int. Cl.$^5$ ............................................ C07C 45/00
[52] U.S. Cl. ............................................ 568/449; 502/158; 502/161; 556/22; 556/404; 556/487; 556/489; 560/177; 560/250; 560/266; 560/97; 562/463; 562/522; 562/406; 564/237; 564/219; 564/342; 568/309; 568/338; 568/396; 568/426; 568/451; 568/454; 568/629; 568/880
[58] Field of Search ............... 568/451, 655, 452, 454, 568/881, 426, 88 D, 309, 338, 383, 396, 449, 629, 579; 502/404, 158; 560/76, 897; 556/22, 18, 19; 564/463; 562/869

[56] References Cited

U.S. PATENT DOCUMENTS

| | | | |
|---|---|---|---|
| 3,385,886 | 5/1968 | Nicholson et al. | 260/515 |
| 3,904,682 | 9/1975 | Fried et al. | 260/520 |
| 4,239,914 | 12/1980 | Campolmi et al. | 562/466 |
| 4,268,688 | 5/1981 | Tinker et al. | 560/177 |
| 4,306,082 | 12/1981 | Brunner et al. | 568/17 |
| 4,329,507 | 5/1982 | Takeda et al. | 568/332 |
| 4,438,033 | 3/1984 | Botteghi et al. | 260/239.55 |
| 4,439,618 | 3/1984 | Cometti et al. | 560/56 |
| 4,482,749 | 11/1984 | Dennis et al. | 568/454 |
| 4,496,768 | 1/1985 | Dennis et al. | 568/454 |
| 4,567,306 | 1/1986 | Dennis et al. | 568/455 |
| 4,593,126 | 6/1986 | Cornils et al. | 568/454 |
| 4,599,206 | 7/1986 | Billig et al. | 558/85 |
| 4,642,388 | 2/1987 | Young | 568/454 |
| 4,654,176 | 3/1987 | Dang et al. | 260/505 R |
| 4,668,651 | 5/1987 | Billig et al. | 502/158 |
| 4,690,912 | 9/1987 | Paulik et al. | 502/161 |
| 4,694,100 | 9/1987 | Shimizu et al. | 560/105 |
| 4,709,089 | 11/1987 | Shimizu et al. | 562/494 |
| 4,717,775 | 1/1988 | Billig et al. | 568/454 |
| 4,736,061 | 4/1988 | Piccolo et al. | 562/466 |
| 4,737,588 | 4/1988 | Billig et al. | 556/12 |
| 4,748,261 | 5/1988 | Billig et al. | 556/404 |
| 4,769,498 | 9/1988 | Billig et al. | 568/454 |
| 4,774,361 | 9/1988 | Maher et al. | 568/454 |
| 4,795,727 | 1/1989 | Bach et al. | 502/161 |
| 4,801,754 | 1/1989 | Bach et al. | 568/454 |
| 4,814,494 | 3/1989 | Shimizu et al. | 562/419 |
| 4,864,063 | 9/1989 | Piccolo et al. | 568/328 |
| 4,877,908 | 10/1989 | Petit et al. | 568/814 |
| 4,885,376 | 12/1989 | Verkade | 556/18 |
| 4,885,401 | 12/1989 | Billig et al. | 568/454 |
| 4,939,288 | 7/1990 | Talley | 560/81 |
| 4,960,949 | 10/1990 | Devon et al. | 568/454 |
| 4,981,995 | 1/1991 | Elango et al. | 562/406 |
| 4,990,658 | 2/1991 | Stahly et al. | 562/406 |
| 4,994,427 | 2/1991 | Davis et al. | 502/166 |
| 4,996,366 | 2/1991 | Tinucci et al. | 568/454 |
| 5,053,533 | 10/1991 | Giordano et al. | 562/466 |
| 5,059,710 | 10/1992 | Lin et al. | 562/406 |
| 5,059,710 | 10/1988 | Abatjoglou | 568/454 |
| 5,099,077 | 3/1992 | Petit et al. | 568/814 |
| 5,113,022 | 5/1992 | Abatjoglou | 568/454 |

FOREIGN PATENT DOCUMENTS

| | | | |
|---|---|---|---|
| 1027141 | 2/1978 | Canada | 260/565 |
| 117156 | 8/1984 | European Pat. Off. | C07F 9/50 |
| 460905 | 12/1991 | European Pat. Off. | |
| 2208872 | 6/1974 | France | C07C 45/00 |

(List continued on next page.)

OTHER PUBLICATIONS

Wink, Donald J. et al., Inorg. Chem. 1990, 29, 5006–5008.

(List continued on next page.)

*Primary Examiner*—Werren B. Lone
*Attorney, Agent, or Firm*—Gerald L. Coon

[57] ABSTRACT

This invention relates to asymmetric syntheses in which a prochiral or chiral compound is contacted in the presence of an optically active metal-ligand complex catalyst to produce an optically active product.

12 Claims, No Drawings

ASYMMETRIC SYNTHESES

This application is a continuation-in-part of U.S. patent application Ser. No. 07/748,112, filed Aug. 21, 1991, and U.S. patent application Ser. No. 07/748,111, filed Aug. 21, 1991 now abandoned.

RELATED APPLICATIONS

The following are related, commonly assigned applications, filed on Aug. 21, 1991:

U.S. patent application Ser. No. 07/748,111 and U.S. patent application Ser. No. 07/748,112; both of which are incorporated herein by reference.

BRIEF SUMMARY OF THE INVENTION

1. Technical Field

This invention relates to asymmetric syntheses in which a prochiral or chiral compound is contacted in the presence of an optically active metal-ligand complex catalyst to produce an optically active product.

2. Background of the Invention

Asymmetric synthesis is of importance, for example, in the pharmaceutical industry, since frequently only one optically active isomer (enantiomer) is therapeutically active. An example of such a pharmaceutical product is the non-steroidal anti-inflammatory drug naproxen. The S enantiomer is a potent anti-arthritic agent while the R enantiomer is a liver toxin. It is therefore oftentimes desirable to selectively produce one particular enantiomer over its mirror image.

It is known that special precautions must be taken to ensure production of a desired enantiomer because of the tendency to produce optically inactive racemic mixtures, that is equal amounts of each mirror image enantiomer whose opposite optical activities cancel out each other. In order to obtain the desired enantiomer or mirror image stereoisomer from such a racemic mixture, the racemic mixture must be separated into its optically active components. This separation, known as optical resolution, may be carried out by actual physical sorting, direct crystallization of the racemic mixture, or other methods known in the art. Such optical resolution procedures are often laborious and expensive as well as destructive to the desired enantiomer. Due to these difficulties, increased attention has been placed upon asymmetric synthesis in which one of the enantiomers is obtained in significantly greater amounts. Efficient asymmetric synthesis desirably affords the ability to control both regioselectivity (branched/normal ratio), e.g., hydroformylation, and stereoselectivity.

Various asymmetric synthesis catalysts have been described in the art. For example, Wink, Donald J. et al., Inorg. Chem. 1990, 29, 5006–5008 discloses syntheses of chelating bis(dioxaphospholane) ligands through chlorodioxaphospholane intermediates and the demonstration of catalytic competence of bis(phosphite)rhodium cations. A complex derived from dihydrobenzoin was tested as a precursor in the hydroformylation of olefins and gave a racemic mixture. Catonic rhodium complexes of bis(dioxaphospholane) ligands were tested in the hydrogenation of enamides and gave enantiomeric excesses on the order of 2–10%.

Pottier, Y. et al., Journal of Organometallic Chemistry, 370, 1989, 333–342 describes the asymmetric hydroformylation of styrene using rhodium catalysts modified with aminophosphinephosphinite ligands. Enantioselectivities greater than 30% are reportedly obtained.

East Germany Patent Nos. 275,623 and 280,473 relate to chiral rhodium carbohydrate-phosphinite catalyst production. The catalysts are stated to be useful as stereospecific catalysts for carrying out carbon-carbon bond formation, hydroformylation, hydrosilylation, carbonylation and hydrogenation reactions to give optically active compounds.

Stille, John K. et al., Organometallics 1991, 10, 1183–1189 relates to the synthesis of three complexes of platinum II containing the chiral ligands 1-(tert-butoxycarbonyl)-(2S, 4S)-2-[(diphenylphosphino)methyl]-4-(dibenzophospholyl)pyrrolidine, 1-(tert-butoxycarbonyl)-(2S,4S)-2-[(dibenzophospholyl)methyl]-4-(diphenylphosphino)pyrrolidine and 1-(tert-butoxycarbonyl)-(2S,4S)-4-(dibenzophospholyl)-2-[(dibenzophospholyl)methyl]pyrrolidine. Asymmetric hydroformylation of styrene was examined with use of platinum complexes of these three ligands in the presence of stannous chloride as catalyst. Various branched/normal ratios (0.5–3.2) and enantiomeric excess values (12–77%) were obtained. When the reactions were carried out in the presence of triethyl orthoformate, all four catalysts gave virtually complete enantioselectivity (ee>96%) and similar branched/normal ratios.

The search for more effective asymmetric synthesis processes is a constant one in the art. It would be desirable if asymmetric synthesis processes could be provided having good yields of optically active products without the need for optical resolution. It would be further desirable if asymmetric synthesis processes could be provided having the characteristics of high stereoselectivity, high regioselectivity, e.g., hydroformylation, and good reaction rate.

SUMMARY OF THE INVENTION

This invention relates to asymmetric syntheses in which a prochiral or chiral compound is reacted in the presence of an optically active metal-ligand complex catalyst to produce an optically active product.

The processes of this invention are distinctive in that they provide good yields of optically active products having high stereoselectivity, high regioselectivity, e.g., hydroformylation, and good reaction rate without the need for optical resolution. The processes of this invention stereoselectively produce a chiral center. An advantage of this invention is that optically active products can be synthesized from optically inactive reactants. Another advantage is that yield losses associated with the production of an undesired enantiomer can be substantially reduced.

The asymmetric syntheses processes of this invention are useful for the production of numerous optically active organic compounds, e.g., aldehydes, alcohols, ethers, esters, amines, amides, carboxylic acids and the like, which have a wide variety of applications.

This invention also relates to optically active ligands having the formula

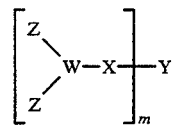

wherein each W is the same or different and is phosphorus, arsenic or antimony, each X is the same or different and is oxygen, nitrogen or a covalent bond linking W and Y, Y is a substituted or unsubstituted hydrocarbon residue, each Z is the same or different and is a substituted or unsubstituted hydrocarbon residue or the Z substituents bonded to W may be bridged together to form a substituted or unsubstituted cyclic hydrocarbon residue, and m is a value equal to the free valence of Y, provided at least one of Y and Z is optically active.

This invention further relates to optically active metal-ligand complex catalysts comprising a metal complexed with an optically active ligand having the formula

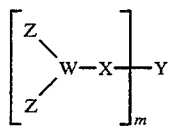

wherein each W is the same or different and is phosphorus, arsenic or antimony, each X is the same or different and is oxygen, nitrogen or a covalent bond linking W and Y, Y is a substituted or unsubstituted hydrocarbon residue, each Z is the same or different and is a substituted or unsubstituted hydrocarbon residue or the Z substituents bonded to W may be bridged together to form a substituted or unsubstituted cyclic hydrocarbon residue, and m is a value equal to the free valence of Y, provided at least one of Y and Z is optically active.

This invention yet further relates to optically active products produced by the asymmetric syntheses of this invention.

DETAILED DESCRIPTION

The subject invention encompasses the carrying out of any known conventional syntheses in an asymmetric fashion in which the catalyst thereof is replaced by an optically active metal-ligand complex catalyst as disclosed herein. Illustrative asymmetric syntheses reactions include, for example, hydroformylation, hydroacylation (intramolecular and intermolecular), hydrocyanation, olefin and ketone hydrosilylation, hydrocarboxylation, hydroamidation, hydroesterification, hydrogenation, hydrogenolysis, aminolysis, alcoholysis, carbonylation, decarbonylation, olefin isomerization, Grignard cross coupling, transfer hydrogenation, olefin hydroboration, olefin cyclopropanation, aldol condensation, allylic alkylation, olefin codimerization, Dieis-Alder reactions and the like. As indicated above, the processes of this invention stereoselectively produce a chiral center. Preferred asymmetric syntheses reactions involve the reaction of organic compounds with carbon monoxide, or carbon monoxide and a third reactant, e.g., hydrogen, in the presence of a catalytic amount of an optically active metal-ligand complex catalyst.

More preferably, the subject invention relates to asymmetric hydroformylation which involves the use of an optically active metal-phosphorus ligand complex catalyst and optionally free ligand in the production of optically active aldehydes wherein a prochiral or chiral olefinic compound is reacted with carbon monoxide and hydrogen. The optically active aldehydes produced correspond to the compounds obtained by the addition of a carbonyl group to an olefinically unsaturated carbon atom in the starting material with simultaneous saturation of the olefinic bond. The processing techniques of this invention may correspond to any of the known processing techniques heretofore employed in conventional asymmetric syntheses reactions including asymmetric hydroformylation reactions.

For instance, the asymmetric syntheses processes can be conducted in continuous, semi-continuous or batch fashion and involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

In general, the asymmetric syntheses reactions are carried out in a liquid reaction medium that contains a solvent for the optically active catalyst, preferably one in which the reaction ingredients including catalyst are substantially soluble. In addition, it may be desired that the asymmetric syntheses processes of this invention be effected in the presence of free ligand as well as in the presence of the optically active complex catalyst. By "free ligand" is meant ligand that is not complexed with the metal atom in the optically active complex catalyst.

As indicated above, the subject invention encompasses the carrying out of any known conventional syntheses in an asymmetric fashion in which the catalyst thereof is replaced by an optically active metal-ligand complex catalyst as disclosed herein.

Asymmetric intramolecular hydroacylation can be carried out in accordance with conventional procedures known in the art. For example, aldehydes containing an olefinic group 3 to 7 carbons removed can be converted to optically active cyclic ketones under hydroacylation conditions in the presence of an optically active metal-ligand complex catalyst described herein.

Asymmetric intermolecular hydroacylation can be carried out in accordance with conventional procedures known in the art. For example, optically active ketones can be prepared by reacting a prochiral olefin and an aldehyde under hydroacylation conditions in the presence of an optically active metal-ligand complex catalyst described herein.

Asymmetric hydrocyanation can be carried out in accordance with conventional procedures known in the art. For example, optically active nitrile compounds can be prepared by reacting a prochiral olefinic compound and hydrogen cyanide under hydrocyanation conditions in the presence of an optically active metal-ligand complex catalyst described herein.

Asymmetric olefin hydrosilylation can be carried out in accordance with conventional procedures known in the art. For example, optically active silyl compounds can be prepared by reacting a prochiral olefin and a silyl compound under hydrosilylation conditions in the presence of an optically active metal-ligand complex catalyst described herein.

Asymmetric ketone hydrosilylation can be carried out in accordance with conventional procedures known in the art. For example, optically active silyl ethers or alcohols can be prepared by reacting a prochiral ketone and a silyl compound under hydrosilylation conditions in the presence of an optically active metal-ligand complex catalyst described herein.

Asymmetric hydrocarboxylation can be carried out in accordance with conventional procedures known in the art. For example, prochiral olefins can be converted to optically active carboxylic acids under hydrocarboxylation conditions in the presence of an optically active metal-ligand complex catalyst described herein.

Asymmetric hydroamidation can be carried out in accordance with conventional procedures known in the art. For example, optically active amides can be prepared by reacting a prochiral olefin, carbon monoxide and a primary or secondary amine or ammonia under hydroamidation conditions in the presence of an optically active metal-ligand complex catalyst described herein.

Asymmetric hydroesterification can be carried out in accordance with conventional procedures known in the art. For example, optically active esters can be prepared by reacting a prochiral olefin, carbon monoxide and an alcohol under hydroesterification conditions in the presence of an optically active metal-ligand complex catalyst described herein.

Asymmetric olefin hydrogenations and other asymmetric hydrogenations can be carried out in accordance with conventional procedures known in the art. For example, hydrogenation can be used to reduce a carbon-carbon double bond to a single bond. Other double bonds can also be hydrogenated, for example, a ketone can be converted to an optically active alcohol under hydrogenation conditions in the presence of an optically active metal-ligand complex catalyst described herein.

Asymmetric hydrogenolysis can be carried out in accordance with conventional procedures known in the art. For example, optically active alcohols can be prepared by reacting an epoxide with hydrogen under hydrogenolysis conditions in the presence of an optically active metal-ligand complex catalyst described herein.

Asymmetric aminolysis can be carried out in accordance with conventional procedures known in the art. For example, optically active amines can be prepared by reacting a prochiral olefin with a primary or secondary amine under aminolysis conditions in the presence of an optically active metal-ligand complex catalyst described herein.

Asymmetric alcoholysis can be carried out in accordance with conventional procedures known in the art. For example, optically active ethers can be prepared by reacting a prochiral olefin with an alcohol under alcoholysis conditions in the presence of an optically active metal-ligand complex catalyst described herein.

Asymmetric carbonylation can be carried out in accordance with conventional procedures known in the art. For example, optically active lactones can be prepared by treatment of allylic alcohols with carbon monoxide under carbonylation conditions in the presence of an optically active metal-ligand complex catalyst described herein.

Asymmetric decarbonylation can be carried out in accordance with conventional procedures known in the art. For example, acyl or aroyl chlorides can be decarbonylated under decarbonylation conditions with retention of configuration in the presence of an optically active metal-ligand complex catalyst described herein.

Asymmetric isomerization can be carried out in accordance with conventional procedures known in the art. For example, allylic alcohols can be isomerized under isomerization conditions to produce optically active aldehydes in the presence of an optically active metal-ligand complex catalyst described herein.

Asymmetric Grignard cross coupling can be carried out in accordance with conventional procedures known in the art. For example, optically active products can be prepared by reacting a chiral Grignard reagent with an alkyl or aryl halide under Grignard cross coupling conditions in the presence of an optically active metal-ligand complex catalyst described herein.

Asymmetric transfer hydrogenation can be carried out in accordance with conventional procedures known in the art. For example, optically active alcohols can be prepared by reacting a prochiral ketone and an alcohol under transfer hydrogenation conditions in the presence of an optically active metal-ligand complex catalyst described herein.

Asymmetric olefin hydroboration can be carried out in accordance with conventional procedures known in the art. For example, optically active alkyl boranes or alcohols can be prepared by reacting a prochiral olefin and a borane under hydroboration conditions in the presence of an optically active metal-ligand complex catalyst described herein.

Asymmetric olefin cyclopropanation can be carried out in accordance with conventional procedures known in the art. For example, optically active cyclopropanes can be prepared by reacting a prochiral olefin and a diazo compound under cyclopropanation conditions in the presence of an optically active metal-ligand complex catalyst described herein.

Asymmetric aldol condensations can be carried out in accordance with conventional procedures known in the art. For example, optically active aldols can be prepared by reacting a prochiral ketone or aldehyde and a silyl enol ether under aldol condensation conditions in the presence of an optically active metal-ligand complex catalyst described herein.

Asymmetric olefin codimerization can be carried out in accordance with conventional procedures known in the art. For example, optically active hydrocarbons can be prepared by reacting a prochiral alkene and an alkene under codimerization conditions in the presence of an optically active metal-ligand complex catalyst described herein.

Asymmetric allylic alkylation can be carried out in accordance with conventional procedures known in the art. For example, optically active hydrocarbons can be prepared by reacting a prochiral ketone or aldehyde and an allylic alkyating agent under alkylation conditions in the presence of an optically active metal-ligand complex catalyst described herein.

Asymmetric Dieis-Alder reaction can be carried out in accordance with conventional procedures known in the art. For example, optically active olefins can be prepared by reacting a prochiral diene and an olefin under cycloaddition conditions in the presence of an optically active metal-ligand complex catalyst described herein.

The permissible prochiral and chiral starting material reactants encompassed by the processes of this invention are, of course, chosen depending on the particular asymmetric syntheses desired. Such starting materials are well known in the art and can be used in conventional amounts in accordance with conventional methods. Illustrative starting material reactants include, for example, substituted and unsubstituted aldehydes (intramolecular hydroacylation, aldol condensation, allylic alkylation), prochiral olefins (hydroformylation, intermolecular hydroacylation, hydrocyanation, hydrosilylation, hydrocarboxylation, hydroamidation, hydroesterification, aminolysis, alcoholysis, cyclopropanation, hydroboration, Dieis-Alder reaction, codimerization), ketones (hydrogenation, hydrosilylation, aldol condensation, transfer hydrogenation, allylic alkylation), chiral and prochiral epoxides (hydroformylation, hydrocyanation, hydrogenolysis), alcohols (carbonylation), acyl and aryl chlorides (decarbonylation), a chiral Grignard reagent (Grignard cross coupling) and the like.

Illustrative olefin starting material reactants useful in certain of the asymmetric syntheses processes of this invention, e.g., hydroformylation, include those which can be terminally or internally unsaturated and be of straight chain, branched-chain or cyclic structure. Such olefins can contain from 4 to 40 carbon atoms or greater and may contain one or more ethylenic unsaturated groups. Moreover, such olefins may contain groups or substituents which do not essentially adversely interfere with the asymmetric syntheses process such as carbonyl, carbonyloxy, oxy, hydroxy, oxycarbonyl, halogen, alkoxy, aryl, haloalkyl, and the like. Illustrative olefinic unsaturated compounds include substituted and unsubstituted alpha olefins, internal olefins, alkyl alkenoates, alkenyl alkanoates, alkenyl alkyl ethers, alkenols and the like, e.g., 1-butene, 1-pentene, 1-hexene, 1-octene, 1-decene, 1-dodecene, 1-octadecene, 2-butene, isoamylene, 2-pentene, 2-hexene, 3-hexene, 2-heptene, cyclohexene, propylene dimers, propylene trimers, propylene tetramers, 2-ethylhexene, 3-phenyl-1-propene, 1,4-hexadiene, 1,7-octadiene, 3-cyclohexyl-1-butene, allyl alcohol, hex-1-en-4-ol, oct-1-en-4-ol, vinyl acetate, allyl acetate, 3-butenyl acetate, vinyl propionate, allyl propionate, allyl butyrate, methyl methacrylate, 3-butenyl acetate, vinyl ethyl ether, vinyl methyl ether, allyl ethyl ether, n-propyl-7-octenoate, 3-butenenitrile, 5-hexenamide, styrene, norbornene, alpha-methylstyrene and the like. Illustrative preferred olefinic unsaturated compounds include, for example, p-isobutylstyrene, 2-vinyl-6-methoxynaphthylene, 3-ethenylphenyl phenyl ketone, 4-ethenylphenyl-2-thienylketone, 4-ethenyl-2fluorobiphenyl, 4-(1,3-dihydro-1-oxo-2H-isoindol-2-yl)styrene, 2-ethenyl-5-benzoylthiophene, 3-ethenylphenyl phenyl ether, propenylbenzene, isobutyl-4-propenylbenzene, phenyl vinyl ether, vinyl chloride and the like. Suitable olefinic unsaturated compounds useful in certain asymmetric syntheses processes of this invention include substituted aryl ethylenes described in U.S. Pat. No. 4,329,507, the disclosure of which is incorporated herein by reference. Of course, it is understood that mixtures of different olefinic starting materials can be employed, if desired, by the asymmetric syntheses processes of the subject invention. More preferably, the subject invention is especially useful for the production of optically active aldehydes, by hydroformylating alpha olefins containing from 4 to 40 carbon atoms or greater and internal olefins containing from 4 to 40 carbon atoms or greater as well as starting material mixtures of such alpha olefins and internal olefins.

Illustrative prochiral and chiral olefins useful in the processes of this invention include those represented by the formula

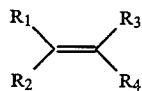

wherein $R_1$, $R_2$, $R_3$ and $R_4$ are the same or different (provided $R_1$ is different from $R_2$ and $R_3$ is different from $R_4$) and are selected from hydrogen; alkyl; substituted alkyl said substitution being selected from amino, including alkylamino and dialkylamino such as benzylamino and dibenzylamino, hydroxy, alkoxy such as methoxy and ethoxy, acyloxy such as acetoxy, halo, nitro, nitrile, thio, carbonyl, carboxamide, carboxaldehyde, carboxyl, carboxyiic ester; aryl including phenyl; substituted aryl including phenyl said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio, said aryl substitution being less than 4 substituents; acyloxy such as acetoxy; alkoxy such as methoxy and ethoxy; amino including alkylamino and dialkylamino such as benzylamino and dibenzyiamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercaptoo It is understood that the prochiral and chiral olefins of this definition also include molecules of the above general formula where the R-groups are connected to form ring compounds, e.g., 3-methyl-l-cyclohexene, and the like.

Illustrative epoxide starting material reactants useful in certain of-the asymmetric syntheses processes of this invention, e.g., hydroformylation, include those represented by the formula

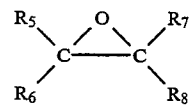

wherein $R_5$, $R_6$, $R_7$ and $R_8$ are the same or different (provided $R_5$ is different from $R_6$ and/or $R_7$ is different from $R_8$) and are selected from hydrogen, monovalent aliphatic or aromatic groups containing 1 to about 12 carbon atoms, and divalent aliphatic groups containing 4 to about 6 carbon atoms in which any permissible combination of $R_5$, $R_6$, $R_7$ and $R_8$ may be linked together to form a substituted or unsubstituted, carbocyclic or heterocyclic ring system such as a monocyclic aromatic or nonaromatic ring system, e.g., cyclohexene oxide. Examples of specific epoxides which are useful in this invention include propylene oxide, 1,2-epoxyoctane, cyclohexene oxide, styrene oxide, and the like.

The optically active catalyst useful in this invention includes an optically active metal-ligand complex catalyst in which the ligand is optically active, preferably optically pure. The permissible metals which make up the optically active metal-ligand complexes include Group VIII metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium and ruthenium, especially rhodium. Other permissible metals include Group IB metals selected from copper (Cu), Silver (Ag), gold (Au) and mixtures thereof, and also Group VIB metals selected from chromium (Cr), molybdenum (Mo), tungsten (W) and mixtures thereof. Mixtures of metals from Group VIII, Group IB and Group VIB may be used in this invention. It is to be noted that the successful practice of this invention does not depend and is not predicated on the exact structure of the optically active metal-ligand complex species, which may be present in their mononuclear, dinuclear and or higher nuclearity forms, provided the ligand is optically active. Indeed, the exact optically active structure is not known. Although it is not intended herein to be bound to any theory or mechanistic discourse, it appears that the optically active catalytic species may in its simplest form consist essentially of the metal in complex combination with the optically active ligand and carbon monoxide when used.

The term "complex" as used herein and in the claims means a coordination compound formed by the union of one or more electronically rich molecules or atoms capable of independent existence with one or more electronically poor molecules or atoms, each of which is also capable of independent existence. For example, the preferred optically active ligands employable herein, i.e., phosphorus ligands, may possess one or more phosphorus donor atoms, each having one available or unshared pair of electrons which are each capable of forming a coordinate covalent bond independently or possibly in concert (e.g., via chelation) with the metal. As can be surmised from the above discussions, carbon monoxide (which is also properly classified as ligand) can also be present and complexed with the metal. The ultimate composition of the optically active complex catalyst may also contain an additional ligand, e.g., hydrogen or an anion satisfying the coordination sites or nuclear charge of the metal. Illustrative additional ligands include, e.g., halogen (Cl, Br, I), alkyl, aryl, substituted aryl, acyl, $CF_3$, $C_2F_5$, CN, $R_2PO$ and $RP(O)(OH)O$ (wherein each R is alkyl or aryl), acetate, acetylacetonate, $SO_4$, $PF_4$, $PF_6$, $NO_2$, $NO_3$, $CH_3O$, $CH_2=CHCH_2$, $C_6H_5CN$, $CH_3CH$, NO, $NH_3$, pyridine, $(C_2H_5)_3N$, mono-olefins, diolefins and triolefins, tetrahydrofuran, and the like. It is of course to be understood that the optically active complex species is preferably free of any additional organic ligand or anion that might poison the catalyst and have an undue adverse effect on catalyst performance. It is preferred in the rhodium catalyzed asymmetric hydroformylation reactions of this invention that the active catalysts be free of halogen and sulfur directly bonded to the rhodium, although such may not be absolutely necessary.

The number of available coordination sites on such metals is well known in the art. Thus the optically active species may comprise a complex catalyst mixture, in their monomeric, dimeric or higher nuclearity forms, which are preferably characterized by at least one phosphorus-containing molecule complexed per one molecule of rhodium. As noted above, it is considered that the optically active species of the preferred rhodium catalyst employed in this invention during asymmetric hydroformylation may be complexed with carbon monoxide and hydrogen in addition to the optically active phosphorus ligands in view-of the carbon monoxide and hydrogen gas employed by the asymmetric hydroformylation process.

Moreover, regardless of whether one preforms the optically active complex catalyst prior to introduction into the reaction zone or whether the active species is prepared in situ during the reaction, the asymmetric syntheses processes and especially the asymmetric hydroformylation reaction may be effected in the presence of free ligand, although such may not be absolutely necessary.

The ligands employable in this invention include those optically active ligands having the general formula

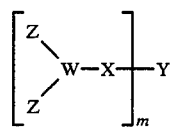

wherein each W is the same or different and is phosphorus, arsenic or antimony, each X is the same or different and is oxygen, nitrogen or a covalent bond linking W and Y, Y is an m-valent substituted or unsubstituted hydrocarbon residue, each Z is the same or different and is a substituted or unsubstituted hydrocarbon residue, preferably a hydrocarbon residue containing at least one heteroatom which is bonded to W, or the Z substituents bonded to W may be bridged together to form a substituted or unsubstituted cyclic hydrocarbon residue, preferably a cyclic hydrocarbon residue containing at least 2 heteroatoms which are each bonded to W, and m is a value equal to the free valence of Y, preferably a value of from 1 to 6, provided at least one of Y and Z is optically active.

Referring to the above general formula, it is appreciated that when m is a value of 2 or greater, the ligand may include any combination of permissible cyclic hydrocarbon residues and/or acyclic hydrocarbon residues which satisfy the valence of Y. It is also appreciated that the hydrocarbon residues represented by Z may include one or more heteroatoms and such heteroatom may be directly bonded to W. The optically active ligands included in the above general structure should be easily ascertainable by one skilled in the art.

For purposes of the asymmetric hydroformylation process of this invention, when each W is phosphorus and each X is a covalent bond, then the Z substituents cannot all be hydrocarbon residues having a carbon atom directly bonded to phosphorus. Also, when Y is a substituted 2 carbon aliphatic chain and m is a value of 2 and both W substituents are phosphorus and one X substituent is oxygen and the other X substituent is nitrogen, then the Z substituents cannot all be phenyl. Further, when Y is a substituted tetrahydropyran and m is a value of 2 and both W substituents are phosphorus and the X substituents are both oxygen, then the Z substituents cannot all be aryl.

For purposes of the novel optically active ligands and novel optically active metal-ligand complex catalysts of this invention, when each W is phosphorus and each X is a covalent bond, then the Z substituents cannot all be hydrocarbon residues having a carbon atom directly bonded to phosphorus. Also, when Y is a substituted 2 carbon aliphatic chain and m is a value of 2 and both W substituents are phosphorus and one X substituent is oxygen and the other X substituent is nitrogen, then the Z substituents cannot all be phenyl. Further, when Y is a substituted tetrahydropyran and m is a value of 2 and both W substituents are phosphorus and the X substituents are both oxygen, then the Z substituents cannot all be aryl. Still further, when Y is an unsubstituted 3 carbon aliphatic chain and m is a value of 2 and both X substituents are oxygen and both W substituents are phosphorus, then the Z substituents bonded to each phosphorus cannot be bridged together to form substituted -ocy-ethylene-oxy- groups.

Illustrative optically active ligands employable in this invention include those of the formulae

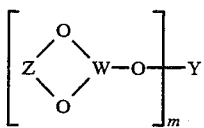

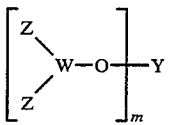

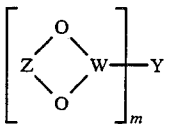

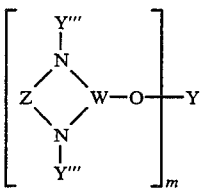

wherein W, Y, Z and m are as defined hereinabove and Y''' is the same or different and is hydrogen or a substituted or unsubstituted hydrocarbon residue. Illustrative preferred optically active ligands encompassed by the above formulae include, for example, (poly)phosphites, (poly)phosphinites, (poly)phosphonites and the like.

Illustrative preferred optically active ligands employable in this invention include the following:

(i) optically active polyphosphites having the formula

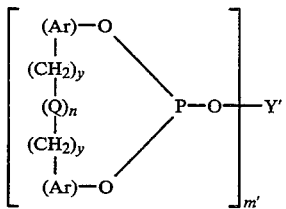

wherein each Ar group is the same or different and is a substituted or unsubstituted aryl radical; Y' is an m-valent substituted or unsubstituted hydrocarbon radical selected from alkylene, alkylene-oxyalkylene, arylene and arylene-$(CH_2)_y$—$(Q)_n$—$(CH_2)_y$—arylene; each y is the same or different and is a value of 0 or 1; each n is the same or different and is a value of 0 or 1; each Q is the same or different and is a substituted or unsubstituted divalent bridging group selected from —$CR^1R^2$—, —O—, —S—, —$NR^3$—, —$SiR^4R^5$— and —CO—, wherein $R^1$ and $R^2$ are the same or different and are hydrogen or a substituted or unsubstituted radical selected from alkyl of 1 to 12 carbon atoms, phenyl, tolyl and anisyl, and $R^3$, $R^4$ and $R^5$ are the same or different and are a radical selected from hydrogen or methyl; and m' is a value of from 2 to 6;

(ii) optically active diorganophosphites having the formula

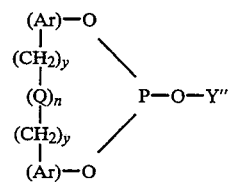

wherein Y'' is a substituted or unsubstituted monovalent hydrocarbon radical and At, Q, n and y are as defined above; and (iii) optically active open-ended bisphosphites having the formula

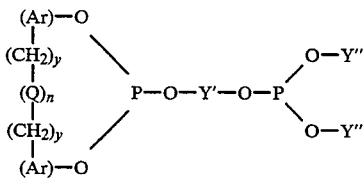

wherein Ar, Q, n, y, Y' and Y'' are as defined above and Y'' can be the same or different.

Illustrative aryl radicals of the above-defined Ar and Y' groups of the above formulae include aryl moieties which may contain from 6 to 18 carbon atoms such as phenylene, naphthylene, anthracylene and the like.

In the above formulae, preferably m is from 2 to 4 and each y and each n has a value of 0. However, when n is 1, Q preferably is a —$CR^1R^2$— bridging group as defined above and more preferably methylene (—$CH_2$—) or alkylidene (—$CHR_2$—), wherein $R^2$ is an alkyl radical of 1 to 12 carbon atoms (e.g., methyl, ethyl, propyl, isopropyl, butyl, dodecyl, etc.), especially methyl.

The m-valent hydrocarbon radicals represented by Y' in the polyphosphite ligand formula above are hydrocarbons containing from 2 to 30 carbon atoms selected from alkylene, alkylene-oxy-alkylene, arylene, and arylene-(—$CH_2$—)$_y$—$(Q)_n$—(—$CH_2$—)$_y$— arylene radicals, wherein Q, n and y are the same as defined above. Preferably the alkylene moieties of said radicals contain from 2 to 18 carbon atoms and more preferably from 2 to 12 carbon atoms, while the arylene moieties of said radicals preferably contain from 6 to 18 carbon atoms.

The divalent bridging group represented by Y' in the open-ended bisphosphite ligand formula above are divalent hydrocarbons containing from 2 to 30 carbon atoms selected from alkylene, alkylene-oxy-alkylene, arylene and arylene-(—$CH_2$—)$_y$—$(Q)_n$—(—$CH_2$—)$_y$-arylene radicals, wherein Q, n and y are the same as defined above. Preferably the alkylene moieties of said radicals contain from 2 to 18 carbon atoms and more preferably from 2 to 12 carbon atoms, while the arylene moieties of said radicals preferably contain from 6 to 18 carbon atoms.

Hydrocarbon radicals represented by Y'' in the above phosphite ligand formulae include monovalent hydrocarbon radicals containing from 1 to 30 carbon atoms selected from alkyl radicals including linear or branched primary, secondary or tertiary alkyl radicals, such as methyl, ethyl, n-propyl, isopropyl, amyl, sec-amyl, t-amyl, 2-ethylhexyl and the like; aryl radicals such as phenyl, naphthyl and the like; aralkyl radicals such as benzyl, phenylethyl, tri-phenylmethylethane and the like; alkaryl radicals such as tolyl, xylyl and the like; and cycloalkyl radicals such as cyclopentyl, cyclohexyl, cyclohexylethyl and the like.

Preferably, Y'' is selected from alkyl and aryl radicals which contain from about 1 and 30 carbon atoms. Preferably, the alkyl radicals contain from 1 to 18 carbon atoms, most preferably from 1 to 10 carbon atoms, while the aryl, aralkyl, alkaryl and cycloalkyl radicals preferably contain from 6 to 18 carbon atoms. Further, although each Y'' group in the open-ended bisphosphite ligand formula above may differ from the other, preferably they are identical.

Of course, it is, to be further understood that the aryl moieties in the above formulae may also be substituted with any substituent radical that does not unduly adversely affect the processes of this invention. Illustrative substituents include radicals containing from 1 to 18 carbon atoms such as alkyl, aryl, aralkyl, alkaryl and cycloalkyl radicals; alkoxy radicals; silyl radicals such as $-Si(R^9)_3$ and $-Si(OR^9)_3$; amino radicals such as $-N(R^9)_2$; acyl radicals such as $-C(O)R^9$; acyloxy radicals such as $-OC(O)R^9$; carbonyloxy radicals such as $-COOR^9$; amido radicals such as $-C(O)N(R^9)_2$ and $-N(R^9)COR^9$; sulfonyl radicals such as $-SO_2R^9$; sulfinyl radicals such as $-SO(R^9)_2$; thionyl radicals such as $-SR^9$; phosphonyl radicals such as $-P(O)(R^9)_2$; as well as halogen, nitro, cyano, trifluoromethyl and hydroxy radicals and the like, wherein each $R^9$ can be a monovalent hydrocarbon radical such as alkyl, aryl, alkaryl, aralkyl and cycloalkyl radicals, with the provisos that in amino substitutents such as $-N(R^9)_2$, each $R^9$ taken together can also comprise a divalent bridging group that forms a heterocyclic radical with the nitrogen atom, in amido substituents such as $-C(O)N(R^9)_2$ and $-N(R^9)COR^9$, each $R^9$ bonded to N can also be hydrogen, and in phosphonyl substituents such as $-P(O)(R^9)_2$, one $R^9$ can be hydrogen. It is to be understood that each $R^9$ group in a particular substituent may be the same of different. Such hydrocarbon substituent radicals could possibly in turn be substituted with a substituent such as already herein outlined above provided that any such occurrence would not unduly adversely effect the processes of this invention. At least one ionic moiety selected from salts of carboxylic acid and of sulfonic acid may be substituted on an aryl moiety in the above formulae.

Among the more preferred phosphite ligands are those wherein the two Ar groups linked by the bridging group represented by $-(CH_2)_y-(Q)_n-(CH_2)_y-$ in the above formulae are bonded through their ortho positions in relation to the oxygen atoms that connect the Ar groups to the phosphorus atom. It is also preferred that any substituent radical, when present on such Ar groups, be bonded in the para and/or ortho position on the aryl in relation to the oxygen atom that bonds the substituted Ar group to its phosphorus atom.

Illustrative monovalent hydrocarbon residues represented by the Z, Y, Y'' and Y''' groups in the above formulae include substituted or unsubstituted monovalent hydrocarbon radicals containing from 1 to 30 carbon atoms selected from substituted or unsubstituted alkyl, aryl, alkaryl, aralkyl and alicyclic radicals. While each Z and Y'' group in a given formula may be individually the same or different, preferably they are both the same.

More specific illustrative monovalent hydrocarbon residues represented by Z, Y, Y'' and Y'''include primary, secondary and tertiary chain alkyl radicals such as methyl, ethyl, propyl, isopropyl, butyl, sec-butyl, t-butyl, neo-pentyl, sec-amyl, t-amyl, iso-octyl, 2-ethylhexyl, iso-nonyl, iso-decyl, octadecyl and the like; aryl radicals such as phenyl, naphthyl, anthracyl and the like; aralkyl radicals such as benzyl, phenylethyl and the like; alkaryl radicals such as tolyl, xylyl, p-alkylphenyls and the like; and alicyclic radicals such as cyclopentyl, cyclohexyl, cyclooctyl, cyclohexylethyl, 1-methylcyclohexyl and the like. Preferably the unsubstituted alkyl radicals may contain from 1 to 18 carbon atoms, more preferably from 1 to 10 carbon atoms, while the unsubstituted aryl, aralkyl, alkaryl and alicyclic radicals preferably contain from 6 to 18 carbon atoms. Among the more preferred Z, Y, Y'' and Y''' residues are phenyl and substituted phenyl radicals.

Illustrative divalent hydrocarbon residues represented by Z, Y and Y' in the above formulae include substituted and unsubstituted radicals selected from alkylene, -alkylene-oxy-alkylene-, arylene, -arylene-oxy-arylene-, alicyclic radicals, phenylene, naphthylene, -arylene-$(CH_2)_y(Q)_n(CH_2)_y$— arylene- such as -phenylene-$(CH_2)_y(Q)_n(CH_2)_y$— phenylene- and -naphthylene—$(CH_2)_y(Q)_n(CH_2)_y$— naphthylene- radicals, wherein Q, y and n are as defined hereinabove. More specific illustrative divalent radicals represented by Z, Y and Y' include, e.g., 1,2-ethylene, 1,3-propylene, 1,6-hexylene, 1,8-octylene, 1,12-dodecylene, 1,4-phenylene, 1,8-naphthylene, 1,1'-biphenyl-2,2'-diyl, 1,1'-binaphthyl-2,2'-diyl, 2,2'-binaphthyl-1,1'-diyl and the like. The alkylene radicals may contain from 2 to 12 carbon atoms, while the arylene radicals may contain from 6 to 18 carbon atoms. Preferably Z is an arylene radical, Y is an alkylene radical and Y' is an alkylene radical.

Moreover, the above-described radicals represented by Z, Y, Ar, Y' and Y'' of the above formulae, may be further substituted with any substituent that does not unduly adversely effect the desired results of this invention. Illustrative substituents are, for example, monovalent hydrocarbon radicals having between one and about 18 carbon atoms, such as alkyl, aryl, alkaryl, aralkyl, cycloalkyl and other radicals as defined above. In addition, various other substituents that may be present include, e.g., halogen, preferably chlorine or fluorine, $-NO_2$, $-CN$, $-CF_3$, $-OH$, $-Si(CH_3)_3$, $-Si(OCH_3)_3$, $-Si(C_3H_7)_3$, $-C(O)$ $CH_3$, $-C(O)C_2H_5$, $-OC(O)C_6H_5$, $-C(O)OCH_3$, $-N(CH_3)_2$, $-NH_2$, $-NHCH_3$, $-NH(C_2H_5)$, $-CONH_2$, $-CON(CH_3)_2$, $-S(O)_2C_2H_5$, $-OCH_3$, $-OC_2H_5$, $-OC_6H_5$, $-C(O)C_6H_5$, $-O(t-C_4H_9)$, $-SC_2H_5$, $-OCH_2CH_2OCH_3$, $-(OCH_2CH_2)_2OCH_3$, $-(OCH_2CH_2)_3OCH_3$, $-SCH_3$, $-S(O)CH_3$, $-SC_6H_5$, $-P(O)(C_6H_5)_2$, $-P(O)(CH_3)_2$, $-P(O)(C_2H_5)_2$, $-P(O)(C_3H_7)_2$, $-P(O)(C_4H_9)_2$, $-P(O)(C_6H_{13})_2$, $-P(O)CH_3(C_6H_5)$, $-P(O)(H)(C_6H_5)$, $-NHC(O)CH_3$ and the like. Moreover, each Z, Y, Ar, Y' and Y'' group may contain o ne or more such substituent groups which may also be t he same-or different in any given ligand molecule. Pr eferred substituent radicals include alkyl and alkoxy radicals containing from 1 to 18 carbon atoms and more preferably from 1 to 10 carbon atoms, especially t-butyl and methoxy.

The optically active ligands employed in the complex catalysts of this invention are uniquely adaptable and suitable for asymmetric syntheses processes, especially rhodium catalyzed asymmetric hydroformylation. For instance, the optically active phosphorus ligands may provide very good rhodium complex stability in addition to providing good catalytic activity for the asymmetric hydroformylation of all types of permissible olefins. Further, their unique chemical structure should provide the ligand with very good stability against side reactions such as being hydrolyzed during asymmetric hydroformylation, as well as upon storage.

The types of novel optically active ligands of the generic class employable in this invention can be prepared by methods known in the art. For instance, the optically active phosphorus ligands employable in this invention can be prepared via a series of conventional phosphorus halide-alcohol or amine condensation reactions in which at least one of the alcohol or amine ingredients is optically active or optically pure. Such types of condensation reactions and the manner in which they may be conducted are well known in the art. Moreover, the phosphorus ligands employable herein can be readily identified and characterized by conventional analytical techniques, such as Phosphorus-31 nuclear magnetic resonance spectroscopy and Fast Atom Bombardment Mass Spectroscopy if desired.

As noted above, the optically active ligands can be employed as both the ligand of the optically active metal-ligand complex catalyst, as well as, the free ligand that can be present in the reaction medium of the processes of this invention. In addition, it is to be understood that while the optically active ligand of the metal-ligand complex catalyst and any excess free ligand preferably present in a given process of this invention are normally the same type of ligand, different types of optically active ligands, as well as, mixtures of two or more different optically active ligands may be employed for each purpose in any given process, if desired.

The optically active metal-ligand complex catalysts of this invention may be formed by methods known in the art. See, for example, U.S. Pat. Nos. 4,769,498, 4,717,775, 4,774,361, 4,737,588, 4,885,401, 4,748,261, 4,599,206, 4,668,651, 5,059,710 and 5,113,022, all of which are incorporated herein by reference. For instance, preformed metal hydrido-carbonyl catalysts may possibly be prepared and introduced into the reaction medium of an asymmetric syntheses process. More preferably, the metal-ligand complex catalysts of this invention can be derived from a metal catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction medium along with the ligand for the in situ formation of the active catalyst. In a preferred embodiment, rhodium dicarbonyl acetylacetonate is employed as a rhodium precursor and reacted in the presence of a solvent with a phosphorus ligand compound to form a catalytic rhodium-phosphorus complex precursor which is introduced into the reactor, optionally along with excess free phosphorus ligand, for the in situ formation of the active catalyst. In any event, it is sufficient for the purpose of this invention to understand that an optically active metal-ligand complex catalyst is present in the reaction medium under the conditions of the asymmetric syntheses and more preferably asymmetric hyroformylation process.

Moreover, it is clear in that the amount of optically active complex catalyst present in the reaction medium of a given process of this invention need only be that minimum amount necessary to provide the given metal concentration desired to be employed and which will furnish the basis for at least that catalytic amount of metal necessary to catalyze the particular asymmetric syntheses process desired. In general, metal concentrations in the range of from about 1 ppm to about 10,000 ppm, calculated as free metal, and ligand to metal mole ratios in the catalyst ranging from about 0.5:1 to about 200:1, should be sufficient for most asymmetric syntheses processes. Moreover, in the rhodium catalyzed asymmetric hydroformylation processes of this invention, it is generally preferred to employ from about 10 to 1000 ppm of rhodium and more preferably from 25 to 750 ppm of rhodium, calculated as free metal.

A further aspect of this invention can be described as the use in asymmetric syntheses of a catalyst precursor composition consisting essentially of a solubilized metal-ligand complex precursor catalyst, an organic solvent and free ligand. Such precursor compositions may be prepared by forming a solution of a metal starting material, such as a metal oxide, hydride, carbonyl or salt e.g., a nitrate, which may or may,not be in complex combination with an optically active ligand, an organic solvent and a free ligand as defined herein. Any suitable metal starting material may be employed, e.g., rhodium dicarbonyl acetylacetonate, $Rh_2O_3$, $Rh_4(CO)_{12}$, $Rh_6(CO)_{16}$, $Rh(NO_3)_3$, poly-phosphite rhodium carbonyl hydrides, iridium carbonyl, poly-phosphite iridium carbonyl hydrides, osmium halide, chlorosmic acid, osmium carbonyls, palladium hydride, palladous halides, platinic acid, platinous halides, ruthenium carbonyls, as well as other salts of other metals and carboxylates of $C_2$–$C_{16}$ acids such as cobalt chloride, cobalt nitrate, cobalt acetate, cobalt octoate, ferric acetate, ferric nitrate, nickel fluoride, nickel sulfate, palladium acetate, osmium octoate, iridium sulfate, ruthenium nitrate, and the like. Of course, any suitable solvent may be employed such as those employable in the asymmetric syntheses process desired to be carried out. The desired asymmetric syntheses process may of course also dictate the various amounts of metal, solvent and optically active ligand present in the precursor solution. Optically active ligands if not already complexed with the initial metal may be complexed to the metal either prior to or in situ during the asymmetric syntheses process.

By way of illustration, since the preferred metal is rhodium and the preferred optically active ligand is a phosphorus ligand and since the preferred asymmetric syntheses process is hydroformylation, a preferred catalyst precursor composition of this invention can include a solubilized rhodium carbonyl phosphorus complex precursor catalyst, an organic solvent and phosphorus ligand prepared by forming a solution of rhodium dicarbonyl acetylacetonate, an organic solvent and optically active phosphorus ligand as defined herein. The phosphorus readily replaces one or both of the carbonyl ligands of the rhodium-acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium phosphorus complex precursor are soluble can be employed. Accordingly, the amounts of rhodium complex catalyst precursor, organic solvent and optically active phosphorus ligand as well as their preferred embodiments present in such catalyst precursor compositions may obviously correspond to those amounts employable in the asymmetric hydroformylation process of this invention and which have already been discussed herein. It is believed that the acetylacetonate ligand of the precursor catalyst is replaced after the asymmetric hydroformylation process has begun with a different ligand, e.g., hydrogen or carbon monoxide, to form the optically active rhodium complex catalyst as explained above. The acetylacetone which is freed from the precursor catalyst under hydroformylation conditions may be removed from the reaction medium with the product aldehyde and thus is in no way detrimental to the asymmetric hydroformylation process. The use of such preferred rhodium complex catalytic precursor compositions thus provides a simple economical and efficient method of handling the rhodium precursor metal and hydroformylation start-up.

The optically active catalyst may optionally be supported. Advantages of a supported catalyst may include ease of catalyst separation and ligand recovery. Illustrative examples of supports include alumina, silica gel, ion-exchange resins, polymeric supports and the like.

The permissible process conditions employable in the asymmetric processes of this invention are, of course, chosen depending on the particular asymmetric syntheses desired. Such process conditions are well known in the art. All of the asymmetric syntheses processes of this invention can be carried out in accordance with conventional procedures known in the art. Illustrative reaction conditions for conducting the asymmetric syntheses processes of this invention are described, for example, in Bosnich, B., Asymmetric Catalysis, Martinus Nijhoff Publishers, 1986 and Morrison, James D., Asymmetric Synthesis, Vol. 5, Chiral Catalysis, Academic Press, Inc., 1985, both of which are incorporated herein by reference. Depending on the particular process, operating temperatures can range from about −80° C. or less to about 500° C. or greater and operating pressures can range from about 1 psig or less to about 10,000 psig or greater.

The reaction conditions of effecting the preferred asymmetric hydroformylation process of this invention may be those heretofore conventionally used and may comprise a reaction temperature of from about −25° C. or lower to about 200° C. and pressures ranging from about 1 to 10,000 psia. While the preferred asymmetric syntheses process is the hydroformylation of olefinically unsaturated compounds and more preferably olefinic hydrocarbons, with carbon monoxide and hydrogen to produce optically active aldehydes, it is to be understood that the optically active metal-ligand complexes may be employed as catalysts in other types of asymmetric syntheses processes to obtain good results. Moreover, while such other asymmetric syntheses may be performed under their usual conditions, in general it is believed that they may be performed at lower temperatures than normally preferred due to the optically active metal-ligand complex catalysts.

As noted, the preferred process of this invention involves the production of optically active aldehydes via asymmetric hydroformylation of a prochiral or chiral olefinic unsaturated compound with carbon monoxide and hydrogen in the presence of an optically active metal-phosphorus ligand complex catalyst and optionally free phosphorus ligand, especially an optically active rhodium-phosphorus ligand complex catalyst.

Of course, it is to be understood that while the optimization of the reaction conditions necessary to achieve the best results and efficiency desired are dependent upon one's experience in the utilization of the subject invention, only a certain measure of experimentation should be necessary to ascertain those conditions which are optimum for a given situation and such should be well within the knowledge of one skilled in the art and easily obtainable by following the more preferred aspects of this invention as explained herein and/or be simple routine experimentation.

For instance, the total gas pressure of hydrogen, carbon monoxide and olefinic unsaturated starting compound of the preferred asymmetric hydroformylation process of this invention may range from about 1 to about 10,000 psia. More preferably, however, in the asymmetric hydroformylation of prochiral olefins to produce optically active aldehydes, it is preferred that the process be operated at a total gas pressure of hydrogen, carbon monoxide and olefinic unsaturated starting compound of less than about 1500 psia, and more preferably less than about 1000 psia, The minimum total pressure of the reactants is not particularly critical and is limited predominately only by the amount of reactants necessary to obtain a desired rate of reaction. More specifically, the carbon monoxide partial pressure of the asymmetric hydroformylation process of this invention is preferably from about 1 to about 360 psia, and more preferably from about 3 to about 270 psia, while the hydrogen partial pressure is preferably about 15 to about 480 psia and more preferably from about 30 to about 300 psia. In general, the molar ratio of gaseous hydrogen to carbon monoxide may range from about 1:10 to 100:1 or higher, the more preferred hydrogen to carbon monoxide molar ratio being from about 1:1 to about 1:10. Higher molar ratios of carbon monoxide to gaseous hydrogen may generally tend to favor higher branChed/normal ratios.

Further as noted above, the preferred asymmetric hydroformylation process of this invention may be conducted at a reaction temperature from about −25° C. or lower to about 200° C. The preferred reaction temperature employed in a given process will of course be dependent upon the particular olefinic starting material and optically active metal-ligand complex catalyst employed as well as the efficiency desired. Lower reaction temperatures may generally tend to favor higher enantiomeric excesses (ee) and branched/normal ratios. In general, asymmetric hydroformylations at reaction temperatures of about 0° C. to about 120° C. are preferred for all types of olefinic starting materials. More preferably, alpha-olefins can be effectively hydroformylated at a temperature of from about 0° C. to about 90° C. while even less reactive olefins than conventional linear alpha-olefins and internal olefins as well as mixtures of alpha-olefins and internal olefins are effectively and preferably hydroformylated at a temperature of from about 25° C. to about 120° C. Indeed, in the rhodium-catalyzed asymmetric hydroformylation process of this invention, no substantial benefit is seen in operating at reaction temperatures much above 120° C. and such is considered to be less desirable.

The processes are conducted for a period of time sufficient to produce the optically active products. The exact reaction time employed is dependent, in part, upon factors such as temperature, nature and proportion of starting materials, and the like. The reaction time will normally be within the range of from about one-half to about 200 hours or more, and preferably from less than about one to about 10 hours.

As outlined herein, the asymmetric syntheses process and more preferably asymmetric hydroformylation process of this invention can be carried out in either the liquid or gaseous state and involve a batch, continuous liquid or gas recycle system or combination of such systems. A batch system is preferred for conducting the processes of this invention. Preferably, asymmetric hydroformylation of this invention involves a batch homogeneous catalysis process wherein the hydroformylation is carried out in the presence of both free phosphorus ligand and any suitable conventional solvent as further outlined herein.

The asymmetric syntheses processes and preferably asymmetric hydroformylation process of this invention may be conducted in the presence of an organic solvent for the optically active metal-ligand complex catalyst. Depending on the particular catalyst and reactants employed, suitable organic solvents include, for example, alcohols, alkanes, alkenes, alkynes, ethers, aldehydes, ketones, esters, acids, amides, amines, aromatics and the like. Any suitable solvent which does not unduly adversely interfere with the intended asymmetric syntheses process can be employed and such solvents may include those heretofore commonly employed in known metal catalyzed processes. Increasing the dielectric constant or polarity of a solvent may generally tend to favor increased reaction rates. Of course, mixtures of one or more different solvents may be employed if desired. It is obvious that the amount of solvent employed is not critical to the subject invention and need only be that amount sufficient to provide the reaction medium with the particular metal concentration desired for a given process. In general, the amount of solvent when employed may range from about 5 percent by weight up to about 95 percent by weight or more based on the total weight of the reaction medium.

As noted above, the asymmetric syntheses processes and especially the asymmetric hydroformylation process of this invention can be carried out in the presence of free ligand, i.e., ligand that is not complexed with the metal of the optically active metal-ligand complex catalyst employed. While it is preferred to employ a free ligand that is the same as the ligand of the metal-ligand complex catalyst such ligands need not be the same in a given process, but can be different if desired. While the asymmetric syntheses and preferably asymmetric hydroformylation process of this invention may be carried out in any excess amount of free ligand desired, the employment of free ligand may not be absolutely necessary. Accordingly, in general, amounts of ligand of from about 2 to about 100, or higher if desired, moles per mole of metal (e.g., rhodium) present in the reaction medium should be suitable for most purposes, particularly with regard to rhodium catalyzed hydroformylation; said amounts of ligand employed being the sum of both the amount of ligand that is bound (complexed) to the metal present and the amount of free (non-complexed) ligand present. Of course, if desired, make-up ligand can be supplied to the reaction medium of the asymmetric hydroformylation process, at any time and in any suitable manner, to maintain a predetermined level of free ligand in the reaction medium.

The ability to carry out the processes of this invention in the presence of free ligand can be a beneficial aspect of this invention in that it removes the criticality of employing very low precise concentrations of ligand that may be required of certain complex catalysts whose activity may be retarded when even any amount of free ligand is also present during the process, particularly when large scale commercial operations are involved, thus helping to provide the operator with greater processing latitude.

The processes of this invention are useful for preparing substituted and unsubstituted optically active compounds. The processes of this invention stereoselectively produce a chiral center. Illustrative optically active compounds prepared by the processes of this invention include, for example, substituted and unsubstituted alcohols or phenols; amines; amides; ethers or epoxides; esters; carboxylic acids or anhydrides; ketones; olefins; acetylenes; halides or sulfonates; aldehydes; nitriles; and hydrocarbons. Illustrative preferred optically active aldehyde compounds prepared by the asymmetric hydroformylation process of this invention include, for example, S-2-(p-isobutylphenyl)propionaldehyde, S-2-(6-methoxynaphthyl)propionaldehyde, S-2-(3-benzoylphenyl)propionaldehyde, S-2-(p-thienoylphenyl)propionaldehyde, S-2-(3-fluoro-4-phenyl)phenylpropionaldehyde, S-2-[4-(1,3-dihydro-1-oxo-2H-isoindol-2-yl)phenyl]propionaldehyde, S-2-(2-methylacetaldehyde)-5-benzoylthiophene and the like. Illustrative of suitable optically active compounds which can be prepared by the processes of this invention (including derivatives of the optically active compounds as described hereinbelow and also prochiral and chiral starting material compounds as described hereinabove) include those permissible compounds which are described in Kirk-Othmer, Encyclopedia of Chemical Technology, Third Edition, 1984, the pertinent portions of which are incorporated herein by reference, and The Merck Index, An Encyclopedia of Chemicals, Drugs and Biologicals, Eleventh Edition, 1989, the pertinent portions of which are incorporated herein by reference.

The processes of this invention can provide optically active products having very high enantioselectivity and regioselectivity, e.g., hydroformylation. Enantiomeric excesses of preferably greater than 50%, more preferably greater than 75% and most preferably greater than 90% can be obtained by the processes of this invention. Branched/normal molar ratios of preferably greater than 5:1, more preferably greater than 10:1 and most preferably greater than 25:1 can be obtained by the processes, e.g., hydroformylation, of this invention. The processes of this invention can also be carried out at highly desirable reaction rates suitable for commercial use.

The desired optically active products, e.g., aldehydes, may be recovered in any conventional manner. Suitable separation techniques include, for example, solvent extraction, crystallization, distillation, vaporization, wiped film evaporation, falling film evaporation and the like. It may be desired to remove the optically active products from the reaction system as they are formed through the use of trapping agents as described in WO Patent 8/08835.

The optically active products produced by the asymmetric syntheses processes of this invention can undergo further reaction(s) to afford desired derivatives thereof. Such permissible derivatization reactions can be carried out in accordance with conventional procedures known in the art. Illustrative derivatization reactions include, for example, esterification, oxidation of alcohols to aldehydes, N-alkylation of amides, addition of aldehydes to amides, nitrile reduction, acylation of ketones by esters, acylation of amines and the like. For optically active aldehydes prepared by asymmetric hydroformylation, illustrative derivatization reactions include, for example, oxidation to carboxylic acids, reduction to alcohols, aldol condensation to alpha, beta-unsaturated compounds, reductive amination to amines, amination to imines and the like. This invention is not intended to be limited in any manner by the permissible derivatization reactions.

A preferred derivatization reaction involves oxidation of an optically active aldehyde prepared by asymmetric hydroformylation to give the corresponding optically active carboxylic acid. Such oxidation reactions can be carried otu by conventional procedures known in the art. A number of important pharmaceutical compounds can be prepared by this process including, but not limited to, S-ibuprofen, S-naproxen, S-ketoprofen, S-suprofen, S-flurbiprofen, S-indoprofen, S-tiaprofenic acid and the like. Illustrative preferred derivatization, i.e. oxidation, reactions encompassed within the scope of this invention include, for example, the following reactant/aldehyde intermediate/product combinations:

| Reactant | Aldehyde Intermediate | Product |
| --- | --- | --- |
| p-isobutylstyrene | S-2-(p-isobutylphenyl)-propionaldehyde | S-ibuprofen |
| 2-vinyl-6-methoxy-naphthalene | S-2-(6-methoxynaphthyl)-propionaldehyde | S-naproxen |
| 3-ethenylphenyl phenyl ketone | S-2-(3-benzoylphenyl)-propionaldehyde | S-ketoprofen |
| 4-ethenylphenyl-2-thienylketone | S-2-(p-thienoylphenyl)-propionaldehyde | S-suprofen |
| 4-ethenyl-2-fluoro-biphenyl | S-2-(3-fluoro-4-phenyl)-phenylpropionaldehyde | S-flurbiprofen |
| 4-(1,3-dihydro-1-oxo-2H-isoindol-2-yl)-styrene | S-2-[4-(1,3-dihydro-1-oxo-2H-isoindol-2-yl)-phenyl]propionaldehyde | S-indoprofen |
| 2-ethenyl-5-benzoyl-thiophene | S-2-(2-methyl-acetaldehyde)-5-benzoyl-thiophene | S-tiaprofenic acid |
| 3-ethenylphenyl phenyl ether | S-2-(3-phenoxy)propion-aldehyde | S-fenoprofen |
| propenylbenzene | S-2-phenylbutyraldehyde | S-phenetamid, S-butetamate |
| isobutyl-4-propenyl-benzene | S-2-(4-isobutylphenyl)-butyraldehyde | S-butibufen |
| phenyl vinyl ether | S-2-phenoxypropional-dehyde | pheneticillin |
| vinyl chloride | S-2-chloropropional-dehyde | S-2-chloro-propionic acid |
| 2-vinyl-6-methoxy-naphthalene | S-2-(6-methoxynaphthyl)-propionaldehyde | S-naproxol |
| 2-vinyl-6-methoxy-naphthalene | S-2-(6-methoxynaphthyl)-propionaldehyde | S-naproxen sodium |
| 5-(4-hydroxy)benzoyl-3H-pyrrolizine | 5-(4-hydroxy)benzoly-1-formyl-2,3-dihydro-pyrrolizine | ketorolac or derivative |

Illustrative of suitable reactants in effecting the asymmetric syntheses processes of this invention include by way of example:

AL—alcohols
PH—phenols
TPH—thiophenols
MER—mercaptans
AMN—amines
AMD—amides
ET—ethers
EP—epoxides
ES—esters
H—hydrogen
CO—carbon monoxide
HCN—hydrogen cyanide
HS—hydrosilane
W—water
GR—Grignard reagent
AH—acyl halide
UR—ureas
OX—oxalates
CN—carbamates
CNA—carbamic acids
CM—carbonates
CMA—carbonic acids
CA—carboxylic acids
ANH—anhydrides
KET—ketones
OLE—olefins
ACE—acetylenes
HAL—halides
SUL—sulfonates
ALD—aldehydes
NIT—nitriles
HC—hydrocarbons
DZ—diazo compounds
BOR—boranes
ESE—enol silyl ethers Illustrative of suitable optically active products prepared by the asymmetric syntheses processes of this invention include by way of example:

AL—alcohols
PH—phenols
TPH—thiophenols
MER—mercaptans
AMN—amines
AMD—amides
ET—ethers
EP—epoxides
ES—esters
H—hydrogen
CO—carbon monoxide
SI—silanes
UR—ureas
OX—oxalates
CN—carbamates
CNA—carbamic acids
CM—carbonates
CMA—carbonic acids
CA—carboxylic acids
ANH—anhydrides
KET—ketones
OLE—olefins
ACE—acetylenes
HAL—halides
SUL—sulfonates
ALD—aldehydes
NIT—nitriles
HC—hydrocarbons
CYP—cyclopropanes
ABR—alkylboranes
ADL—aldols Illustrative of permissible asymmetric syntheses reactions encompassed within the scope of this invention include, for example, the following reactant/product combinations:

| REACTANT(S) | PRODUCT(S) |
| --- | --- |
| OLE, CO, H | ALD |
| OLE, CO, H | CA |
| ALD | KET |
| OLE, ALD | KET |
| OLE, HC | HC |
| OLE, CO | CA |
| OLE, CO, AMN | AMD |
| OLE, CO, AL | ES |

| REACTANT(S) | PRODUCT(S) |
|---|---|
| KET, H | AL |
| EP, H | AL |
| OLE, AMN | AMN |
| OLE, AL | ET |
| AL, CO | HC |
| AL | ALD |
| OLE, HCN | NIT |
| OLE, HS | SI |
| OLE, CO, W | CA |
| OLE | OLE |
| GR | HC |
| AH | HAL |
| OLE, H | HC |
| OLE, BOR | AL |
| OLE, BOR | ABR |
| OLE, DZ | CYP |
| KET, AL | AL |
| ALD, ESE | ADL |
| KET, ESE | ADL |
| KET, HS | AL |
| EP, CO, H | ALD |
| EP, HCN | NIT |

As indicated above, the processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Finally, the optically active products of the process of this invention have a wide range of utility that is well known and documented in the prior art, e.g. they are especially useful as pharmaceuticals, flavors, fragrances, agricultural chemicals and the like. Illustrative therapeutic applications, include, for example, non-steroidal anti-inflammatory drugs, ACE inhibitors, beta-blockers, analgesics, bronchodilators, spasmolytics, antihistimines, antibiotics, antitumor agents and the like.

As used herein, the following terms have the indicated meanings:

chiral—molecules which have one or more centers of asymmetry.

achiral—molecules or processes which do not include or involve at least one center of asymmetry.

prochiral—molecules which have the potential to be converted to a chiral product in a particular process.

chiral center—any structural feature of a molecule that is a site of asymmetry.

racemic—a 50/50 mixture of two enantiomers of a chiral compound.

stereoisomers—compounds which have identical chemical constitution, but differ as regards the arrangement of the atoms or groups in space.

enantiomer—stereoisomers which are non-superimposable mirror images of one another.

stereoselective—a process which produces a particular stereoisomer in favor of others.

enantiomeric excess (ee)—a measure of the relative amounts of two enantiomers present in a product. ee may be calculated by the formula [amount of major enantiomer− amount of minor enantiomer]/[amount of major enantiomer+ amount of minor enantiomer].

optical activity—an indirect measurement of the relative amounts of stereoisomers present in a given product. Chiral compounds have the ability to rotate plane polarized light. When one enantiomer is present in excess over the other, the mixture is optically active.

optically active—a mixture of stereoisomers which rotates plane polarized light due to an excess of one of the stereoisomers over the others.

optically pure—a single stereoisomer which rotates plane ploarized light.

regioisomers—compounds which have the same molecular formula but differing in the connectivity of the atoms.

regioselective—a process which favors the production of a particular regioisomer over all others.

isoBHA chloridite—1,1'-biphenyl-3,3'-di-t-butyl-5,5'-dimethoxy-2,2'-diylchlorophosphite.

BHA dichloridite—2-t-butyl-4-methoxyphenyl dichlorophosphite.

isoBHT chloridite—1,1'-biphenyl-3,3',5,5'-tetra-t-butyl-2,2'-diylchlorophosphite.

biphenol chloridite—1,1'-biphenyl-2,2'-diylchlorophosphite.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Certain of the following examples are provided to further illustrate the processes of this invention.

EXAMPLE 1

Preparation of (iSOBHA-P)₂-2R,4R-pentanediol isoBHA chloridite (10.48 g, 0.0248 moles) in toluene (20 ml) was charged to a 500 ml Schlenk flask under a nitrogen atmosphere. This flask was cooled in an ice water bath. A separate solution of 2R,4R-pentanediol (1.29 g, 0.0124 moles) in toluene (100 ml) and triethylamine (4.2 ml, 0.0301 moles) was prepared and transferred to the flask containing the isoBHA chloridite solution via cannula over approximately 15 minutes. When the addition was complete, the ice water bath was removed and the mixture was refluxed for 1.5 hours. After cooling, the solution was filtered to remove solid triethylamine hydrochloride. Toluene solvent was removed in vacuo and the residue was dissolved in approximately 15 ml of acetonitrile. After stirring at room temperature for approximately 30 minutes, white crystals formed. The mixture was filtered and the white solid was washed with several portions of acetonitrile and dried under vacuum to yield (isoBHA-P)₂-2R,4R-Pentanediol (6.8 g, 63% yield) having the formula:

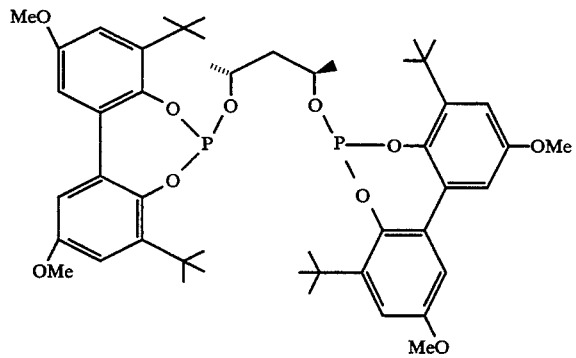

EXAMPLE 2

Preparation of R-binaphthol-BHA diorganophosphite

BHA dichloridite (4.9 g, 0.0175 moles) in toluene (20 ml) was charged to a 250 ml Schlenk flask under a nitrogen atmosphere. This flask was cooled in an ice water bath. A separate solution of R-1,1'-bi-2-naphthol (5 g, 0.0175 moles) in toluene (160 ml) and triethylamine (12 ml, 0.0863 moles) was prepared and transferred to the flask containing the BHA dichloridite solution via cannula over approximately 15 minutes. When the addition was complete, the ice water bath was removed and the mixture was refluxed for 1 hour. Water (40 ml) was added to the reaction mixture to dissolve the triethylamine hydrochloride. The organic layer was separated from the aqueous layer and washed once more with 40 ml of water. The organic layer was separated, toluene solvent was removed in vacuo and the residue was dissolved in approximately 15 ml of acetonitrile. After stirring at room temperature for approximately 30 minutes, white crystals formed. The mixture was filtered and the white solid was washed with several portions of acetonitrile and dried under vacuum to yield R-binaphthol-BHA diorganophosphite (4.2 g, 49% yield) having the formula:

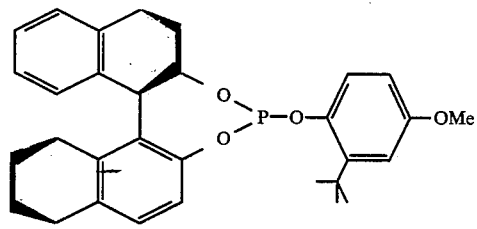

EXAMPLE 3

Preparation of (isoBHT-P)₂-2R,4R-pentanediol isoBHT chloridite (17.3 g, 0.0390 moles) in toluene (100 ml) was charged to a 500 ml Schlenk flask under a nitrogen atmosphere. This flask was cooled in an ice water bath. A separate solution of 2R,4R-pentanediol (1.9 g, 0.0183 moles) in toluene (150 ml) and triethylamine (6 ml, 0.0430 moles) was prepared and transferred to the flask containing the isoBHT chloridite solution via cannula over approximately 15 minutes. When the addition was complete, the ice water bath was removed and the mixture was refluxed for 1.5 hours. After cooling, the solution was filtered to remove solid triethylamine hydrochloride. Toluene solvent was removed in vacuo and the residue was dissolved in approximately 15 ml of acetonitrile. After stirring at room temperature for approximately 30 minutes, white crystals formed. The mixture was filtered and the white solid was washed with several portions of acetonitrile and dried under vacuum to yield (isoBHT-P)₂-2R,4R-Pentanediol (8 g, 48% yield) having the formula:

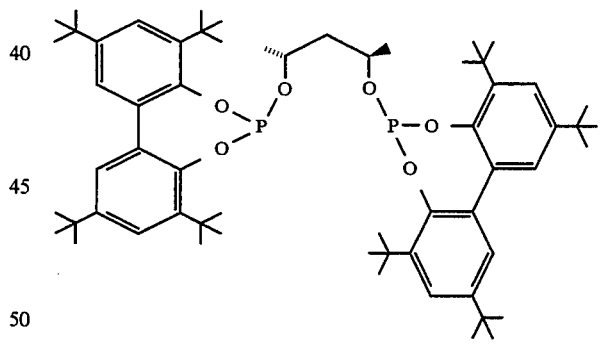

EXAMPLE 4

Preparation of (isoBHA-P)₂-(−)-2,3-O-isopropylidened-threitol isoBHA chloridite (17.2 g, 0.0407 moles) in toluene (20 ml) was charged to a 500 ml Schlenk flask under a nitrogen atmosphere. This flask was cooled in an ice water bath. A separate solution of (-)-2,3-O-isopropylidene-d-threitol (1 g, 0.0124 moles) in toluene (200 ml) and triethylamine (2 ml, 0.0150 moles) was prepared and-transferred to the flask containing the isoBHA chloridite solution via cannula over approximately 15 minutes. When the addition was complete, the ice water bath was removed and the mixture was refluxed for 2 hours. After cooling, the solution was filtered to remove solid triethylamine hydrochloride. Toluene solvent was removed in vacuo and the residue was dissolved in approximately 15 ml of acetonitrile. After stirring at room temperature for approximately 30 minutes, white crystals formed. The mixture was filtered and the white solid was washed with several portions of acetonitrile and dried under vacuum to yield (isoBHA-P)2-(—)-2,3-O-isopropylidene-d-threitol (8.1 g, 70% yield) having the formula:

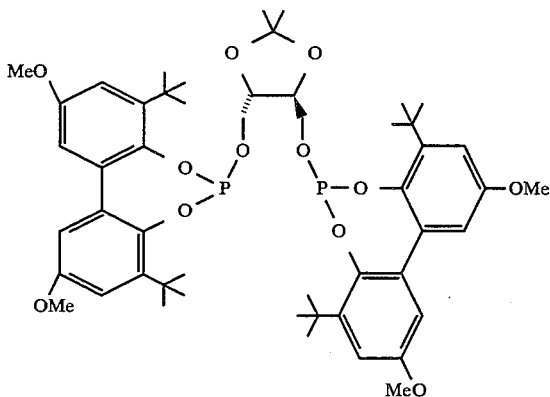

EXAMPLE 5

Preparation of bis(diphenylphosphino)-2R,4R-pentanediol

Chlorodiphenylphosphine (3.5 ml, 0.0195 moles) in toluene (30 ml) was charged to a 500 ml Schlenk flask under a nitrogen atmosphere. This flask was cooled in an ice water bath. A separate solution of 2R,4R-pentanediol (1 g, 0.0096 moles>in toluene (100 ml) and triethylamine (3 ml, 0.0225 moles) was prepared and transferred to the flask containing the chlorodiphenylphosphine solution via cannula over approximately 15 minutes. When the addition was complete, the ice water bath was removed and the mixture was refluxed for 2 hours. After cooling, the solution was filtered to remove solid triethylamine hydrochloride. Toluene solvent was removed in vacuo and the residue was dissolved in approximately 15 ml of acetonitrile. After stirring at room temperature for approximately 30 minutes, white crystals formed. The mixture was filtered and the white solid was washed with several portions of acetonitrile and dried under vacuum to yield bis(diphenylphosphino)-2R,4R-pentanediol (2.5 g, 56% yield) having the formula:

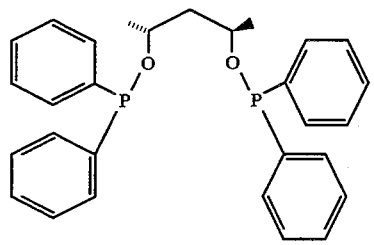

EXAMPLE 6

Preparation of tris(S-1,1'-bi-2-naphthol) bisphosphite

Phosphorus trichloride (0.8 g, 0.0583 moles) in toluene (50 ml) was charged to a 500 ml Schlenk flask under a nitrogen atmosphere. This flask was cooled in an ice water bath. A separate solution of S-1,1'-bi-2-naphthol (5 g, 0.0175 moles) in toluene (200 ml) and triethylamine (4 ml, 0.0301 moles) was prepared and transferred to the flask containing the phosphorus trichloride solution via cannula over approximately 15 minutes. When the addition was complete, the ice water bath was removed and the mixture was refluxed for 2 hours. After cooling, the solution was filtered to remove solid triethylamine hydrochloride. Toluene solvent was removed in vacuo and the residue was dissolved in approximately 15 ml of acetonitrile. After stirring at room temperature for approximately 30 minutes, white crystals formed. The mixture was filtered and the white solid was washed with several portions of acetonitrile and dried under vacuum to yield tris(S-1,1'-bi-2-naphthol) bisphosphite (14.5 g, 54% yield) having the formula:

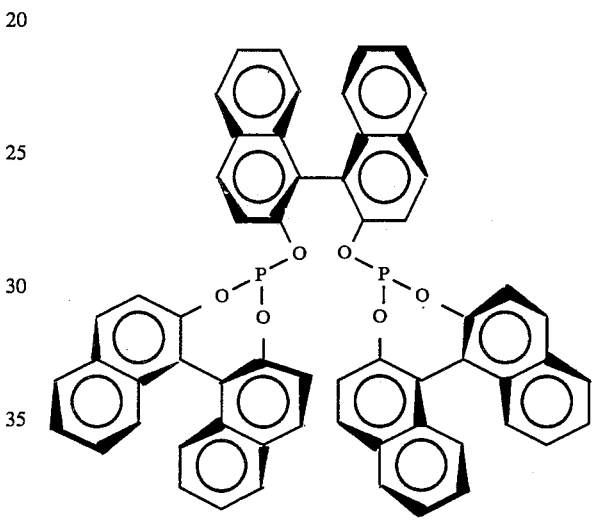

EXAMPLE 7

Preparation of (N,N'-diphenylethylenediamine-P)2-2S, 4S-pentanediol

N,N'-diphenylethylenediaminochlorophosphite (1.99 g, 0.0076 moles) in toluene (20 ml) was charged to a 500 ml Schlenk flask under a nitrogen atmosphere. This flask was cooled in an ice water bath. A separate solution of 2S,4S-pentanediol (0.375 g, 0.0036 moles) in toluene (100 ml) and triethylamine (1 ml, 0.0072 moles) was prepared and transferred to the flask containing the N,N'-diphenylethylenediaminochlorophosphite solution via cannula over approximately 15 minutes. When the addition was complete, the ice water bath was removed and the mixture was refluxed for 1.5 hours. After cooling, the solution was filtered to remove solid triethylamine hydrochloride. Toluene solvent was removed in vacuo and the residue was dissolved in approximately 15 ml of acetonitrile. After stirring at room temperature for approximately 30 minutes, white crystals formed. The mixture was filtered and the white solid was washed with several portions of acetonitrile and dried under vacuum to yield (N,N'-diphenylethylenediamine-P)2-2S,4S-pentanediol (2.0 g, 95% yield) having the formula:

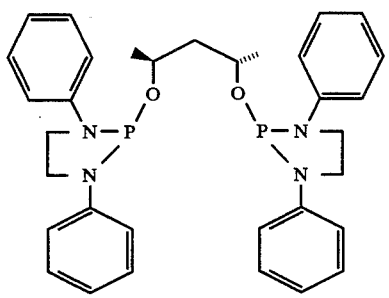

EXAMPLE 8

Preparation of (Biphenol-P)₂-2R,4R-pentanediol

Biphenol chloridite (4.9 g, 0.0196 moles) in toluene (20 ml) was charged to a 500 ml Schlenk flask under a nitrogen atmosphere. This flask was cooled in an ice water bath. A separate solution of 2R,4R-pentanediol (1.02 g, 0.0098 moles) in toluene (100 ml) and triethylamine (3 ml, 0.0216 moles) was prepared and transferred to the flask containing the biphenol chloridite solution via cannula over approximately 15 minutes. When the addition was complete, the ice water bath was removed and the mixture was refluxed for 1.5 hours. After cooling, the solution was filtered to remove solid triethylamine hydrochloride. Toluene solvent was removed in vacuo and the residue was dissolved in approximately 15 ml of acetonitrile. After stirring at room temperature for approximately 30 minutes, white crystals formed. The mixture was filtered and the white solid was washed with several portions of acetonitrile and dried under vacuum to yield (biPhenol-P)₂-2R,4R-Pentanediol (2.12 g, 40% yield) having the formula:

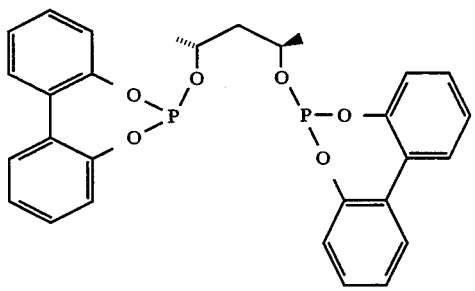

EXAMPLE 9

Preparation of isoBHA-P-S-1,1'-bi-2-naphthol diorganophosphite isoBHA chloridite (4.9 g, 0.0116 moles) in toluene (20 ml) was charged to a 500 ml Schlenk flask under a nitrogen atmosphere. This flask was cooled in an ice-water bath. A separate solution of S-1,1'-bi-2-naphthol (3.32 g, 0.0116 moles) in toluene (100 ml) and triethylamine (1.65 ml, 0.0117 moles) was prepared and transferred to the flask containing the isoBHA chloridite solution via cannula over approximately 15 minutes. When the addition was complete, the ice water bath was removed and the mixture was refluxed for 1.5 hours. After cooling, the solution was filtered to remove solid triethylamine hydrochloride. Toluene solvent was removed in vacuo and the residue was dissolved in approximately 15 ml acetonitrile. After stirring at room temperature for approximately 30 minutes, white crystals formed. The mixture was filtered and the white solid was washed with several portions of acetonitrile and dried under vacuum to yield isoBHA-P-S-1,1'-bi-2-naphthol diorganophosphite (3.3 g, 42.4% yield) having the formula:

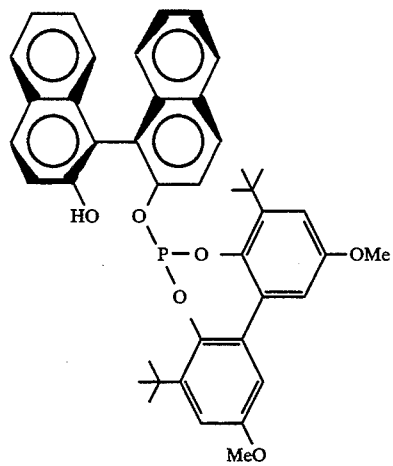

EXAMPLE 10

Preparation of S-1,1'-bi-2-naphthol-P-2,6-di-t-butyl-4-methylphenol diorganophosphite S-1,1'-bi-2-naphthol chloridite (2.09 g, 0.0060 moles) in toluene (20 ml) was charged to a 500 ml Schlenk flask under a nitrogen atmosphere.. This flask was cooled in an ice water bath. A separate solution of 2,6-di-t-butyl-4-methylphenol (1.54 g, 0.0060 moles) in toluene (100 ml) and triethylamine (1 ml, 0.0072 moles) was prepared and transferred to the flask containing the isoBHA chloridite solution via cannula over approximately 15 minutes. When the addition was complete, the ice water bath was removed and the mixture was refluxed for 1.5 hours. After cooling, the solution was filtered to remove solid triethylamine hydrochloride. Toluene solvent was removed in vacuo and the residue was dissolved in approximately 15 ml acetonitrile. After stirring at room temperature for approximately 30 minutes, white crystals formed. The mixture was filtered and the white solid was washed with several portions of acetonitrile and dried under vacuum to yield S-1,1'-bi-2-naphthol-P-2,6-di-t-butyl-4-methylphenol diorganophosphite (1.67 g, 52% yield) having the formula:

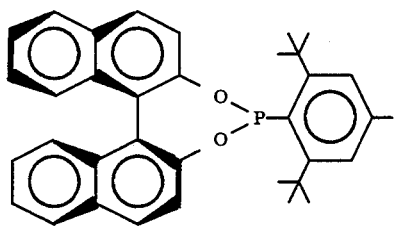

EXAMPLES 11-22

Asymmetric Hydroformylation of Styrene with (isoBHA-P)$_2$-2R,4R-pentanediol/rhodium Catalyst A catalyst solution was prepared consisting of 0.0122 g of rhodium dicarbonyl acetylacetonate (250 ppm rhodium), 0.1702 g of (isoBHA-P)2-2R,4R-pentanediol prepared in Example 1 (4:1 ligand to rhodium ratio) and 19.8 g of toluene. 15 ml of this solution was charged to a 100 ml reactor and heated under nitrogen to 70° C. 1.5 ml of styrene was charged to the reactor and the reactor pressurized to 130 psi with 1:1 syn gas. The rate of the reaction was determined by monitoring the drop in pressure as syn gas was consumed. Reaction rate was approximately 0.26 g-mole/liter/hour. When the rate had slowed due to consumption of the styrene starting material, the reaction mixture was removed from the reactor under a nitrogen atmosphere.

A portion of the reaction mixture was analyzed by gas chromatography to determine product composition. An isomer ratio of 12.4:1 (2-phenylpropionaldehyde:hydrocinnamaldehyde) was observed.

3 ml of the solution was diluted in 50 ml of acetone and treated with 0.3 g of potassium permanganate and 0.32 g of magnesium sulfate to effect oxidation of the product aldehydes to their respective acids. The mixture was stirred at zoom temperature for 30 minutes after which time the solvent was removed under reduced pressure. The residue was extracted three times with 50 ml of hot water. The three aqueous solutions were then combined, filtered and washed with 50 ml of chloroform. The aqueous layer was then acidified with HCl to a pH of 2 and extracted with 50 ml of chloroform. The chloroform was removed in vacuo and the resulting residue dissolved in 0.5 ml of toluene. This solution was analyzed by gas chromotography on a chiral b-cyclodextrin column which could separate the two enantiomers of the resulting 2-phenylpropionic acid. This analysis indicated an 80:20 ratio of the S and R enantiomers for an ee (enantiomeric excess) of 60%.

Table A below summarizes other runs employing this ligand for styrene hydroformylation (all runs at 250 ppm rhodium concentration).

EXAMPLE 23

Asymmetric Hydroformylation of Styrene with R-binaphthol-BHA diorganophosphite/rhodium Catalyst A catalyst solution was prepared consisting of 0.0122 g of rhodium dicarbonyl acetylacetonate (250 ppm rhodium), 0.0480 g of R-binaphthol-BHA diorganophosphite prepared in Example 2 (2:1 ligand to rhodium ratio) and 19.9 g of toluene. 15 ml of this solution was charged to a 100 ml reactor and heated under nitrogen to 45° C. 1.5 ml of styrene was charged to the reactor and the reactor pressurized to 130 psi with 1:1 syn gas. The rate of the reaction was determined by monitoring the drop in pressure as syn gas was consumed. Reaction rate was approximately 0.5 g-mole/liter/hour. When the rate had slowed due to consumption of the styrene starting material, the reaction mixture was removed from the reactor under a nitrogen atmosphere.

A portion of the reaction mixture was analyzed by gas chromatography to determine product composition. An isomer ratio of 6:1 (2-phenylpropionaldehyde:hydrocinnamaldehyde) was observed.

3 ml of the solution was diluted in 50 ml of acetone and treated with 0.3 g of potassium permanganate and 0.32 g of magnesium sulfate to effect oxidation of the product aldehydes to their respective acids. The mixture was stirred at room temperature for 30 minutes after which time the solvent was removed under reduced pressure. The residue was extracted three times with 50 ml of hot water. The three aqueous solutions were then combined, filtered and washed with 50 ml of chloroform. The aqueous layer was then acidified with HCl to a pH of 2 and extracted with 50 ml of chloroform. The chloroform was removed in vacuo and the resulting residue dissolved in 0.5 ml of toluene. This solution was analyzed by gas chromatography on a chiral b-cyclodextrin column which could separate the two enantiomers of the resulting 2-phenylpropionic acid. This analysis indicated an 55:45 ratio of the S and R enantiomers for an ee (enantiomeric excess) of 10%.

EXAMPLES 24-28

Asymmetric Hydroformylation of Styrene with (isoBHT-P)$_2$R,4R-pentanediol/rhodium Catalyst A catalyst solution was prepared consisting of 0.0122 g of rhodium dicarbonyl acetylacetonate (250 ppm rhodium), 0.1907 g of (isoBHT-P)$_2$-2R,4R-pentanediol prepared in Example 3 (4:1 ligand to rhodium ratio) and 19.8 g of toluene. 15 ml of this solution was charged to a 100 ml reactor and heated under nitrogen to 70° C. 1.5 ml of styrene was charged to the reactor and the reactor pressurized to 130 psi with 1:1 syn gas. The rate of the

TABLE A

| Example No. | Solvent | Ligand/Rhodium Mole Ratio | Temp. °C. | Syn Gas Pressure | Syn Gas Mole Ratio | Styrene Conc. | Reaction Rate g moles/liter/hour | Isomer Mole Ratio | ee |
|---|---|---|---|---|---|---|---|---|---|
| 11 | toluene | 4:1 | 70 | 130 psi | 1:1 | 9% | 0.26 | 12.4:1 | 60% |
| 12 | toluene | 4:1 | 70 | 75 psi | 1:1 | 9% | 0.18 | 6.9:1 | 45% |
| 13 | toluene | 4:1 | 70 | 130 psi | 2:1 | 9% | 0.22 | 13.2 | 61% |
| 14 | toluene | 4:1 | 50 | 200 psi | 1:1 | 9% | 0.12 | 18.5:1 | 71% |
| 15 | toluene | 8:1 | 50 | 130 psi | 1:1 | 9% | 0.37 | 27.0:1 | 71% |
| 16 | toluene | 8:1 | 50 | 130 psi | 1:1 | 37.5% | 0.72 | 28.9:1 | 72% |
| 17 | toluene | 8:1 | 25 | 130 psi | 1:1 | 37.5% | 0.30 | 45.3:1 | 81% |
| 18 | toluene | 4:1 | 25 | 500 psi | 1:1 | 37.5% | 0.11 | 49.2:1 | 90% |
| 19 | ethylacetate | 4:1 | 70 | 130 psi | 1:1 | 9% | 0.84 | 14.4:1 | 61% |
| 20 | 3-pentanone | 4:1 | 70 | 130 psi | 1:1 | 9% | 0.94 | 14.2:1 | 66% |
| 21 | acetone | 4:1 | 70 | 130 psi | 1:1 | 9% | 1.03 | 12.9:1 | 66% |
| 22 | p-nitrobenzene | 2:1 | 25 | 130 psi | 1:2.7 | 25% | 1.00 | 91:1 | 85% | reaction was determined by monitoring the drop in pressure as syn gas was consumed. Reaction rate was approximately 0.44 g-mole/liter/hour. When the rate had slowed due to consumption of the styrene starting material, the reaction mixture was removed from the reactor under a nitrogen atmosphere.

A portion of the reaction mixture was analyzed by gas chromatography to determine product composition.

An isomer ratio of 21.2:1 (2-phenylpropionaldehyde:-hydrocinnamaldehyde) was observed.

3 ml of the solution was diluted in 50 ml of acetone and treated with 0.3 g of potassium permanganate and 0.32 g of magnesium sulfate to effect oxidation of the product aldehydes to their respective acids. The mixture was stirred at room temperature for 30 minutes after which time the solvent was removed under reduced pressure. The residue was extracted three times with 50 ml of hot water. The three aqueous solutions were then combined, filtered and washed with 50 ml of chloroform. The aqueous layer was then acidified with HCl to a pH of 2 and extracted with 50 ml of chloroform. The chloroform was removed in vacuo and the resulting residue dissolved in 0.5 ml of toluene. This solution was analyzed by gas chromatography on a chiral b-cyclodextrin column which could separate the two enantiomers of the resulting 2-phenylpropionic acid. This analysis indicated an 62:38 ratio of the S and R enantiomers for an ee (enantiomeric excess) of 44%.

Table B below summarizes other runs employing this ligand for styrene hydroformylation (all runs at 250 ppm rhodium concentration).

17.6 g of toluene. 15 ml of this solution was charged to a 100 ml reactor and heated under nitrogen to 50° C. 1.5 ml of vinyl acetate was charged to the reactor. The reactor was pressurized to 130 psi with 1:1 syn gas. The rate of the reaction was determined by monitoring the drop in pressure as syn gas was consumed. Reaction rate was approximately 0.12 g-mole/liter/hour. When the rate had slowed due to consumption of the norbornene starting material, the reaction mixture was removed from the reactor under a nitrogen atmosphere.

A portion of the reaction mixture was analyzed by gas chromatography to determine product composition. Only a single regioisomer, a-acetoxypropionaldehyde, was obtained.

A second portion of the solution was analyzed on a Cyclodex B column to determine enantioselectivity. A 75:25 distribution of enantiomers, 50% ee, was observed with the S stereoisomer isomer as the major product.

EXAMPLE 31

Asymmetric Hydroformylation of Styrene with (isoBHA-P)$_2$-(−)-2,3-0-isopropylidene-d-threitol/ rhodium Catalyst

TABLE B

| Example No. | Solvent | Ligand/Rhodium Mole Ratio | Temp. °C. | Syn Gas Pressure | Syn Gas Mole Ratio | Styrene Conc. | Reaction Rate g moles/liter/hour | Isomer Mole Ratio | ee |
| --- | --- | --- | --- | --- | --- | --- | --- | --- | --- |
| 24 | toluene | 4:1 | 70 | 130 psi | 1:1 | 9% | 0.44 | 21.2:1 | 44% |
| 25 | toluene | 4:1 | 50 | 130 psi | 1:1 | 9% | 0.23 | 54.5:1 | 61% |
| 26 | toluene | 8:1 | 50 | 130 psi | 1:1 | 9% | 0.31 | 54.3:1 | 67% |
| 27 | toluene | 8:1 | 40 | 130 psi | 1:1 | 9% | 0.14 | 57.6:1 | 66% |
| 28 | acetone | 2:1 | 25 | 130 psi | 4:1 | 25% | 0.10 | 190:1 | 77% |

EXAMPLE 29

Asymmetric Hydroformylation of Norbornene with (isoBHA-p)$_2$-2R,4R-pentanediol/rhodium Catalyst A catalyst solution was prepared consisting of 0.0122 g of rhodium dicarbonyl acetylacetonate (250 ppm rhodium), 0.1702 g of (isoBHA-P)$_2$-2R,4R-pentanediol prepared in Example 1 (4:1 ligand to rhodium ratio), 2.25 g of norbornene and 17.6 g of acetone. 15 ml of this solution was charged to a 100 ml reactor and heated under nitrogen to 50° C. The reactor was pressurized to 130 psi with 1:1 syn gas. The rate of the reaction was determined by monitoring the drop in pressure as syn gas was consumed. Reaction rate was approximately 2.55 g-mole/liter/hour. When the rate had slowed due to consumption of the norbornene starting material, the reaction mixture was removed from the reactor under a nitrogen atmosphere.

A portion of the reaction mixture was analyzed by gas chromatography to determine product composition. Only a single regioisomer, exo-2-norbornaldehyde, was observed.

A second portion of the solution was analyzed on a Chiraldex B-TA column to determine enantioselectivity. An 80:20 distribution of enantiomers, a 60% ee was observed with the exo-1R,2R,4S-norbornaldehyde isomer as the major product.

EXAMPLE 30

Asymmetric Hydroformylation of Vinyl Acetate with (isoBHA-P)$_2$-2R,4R-pentanediol/rhodium Catalyst A catalyst solution was prepared consisting of 0.0122 g of rhodium dicarbonyl acetylacetonate (250 ppm Rhodium), 0.1702 g of (isoBHA-P)$_2$-2R,4R-pentanediol prepared in Example 1 (4:1 ligand to rhodium ratio) and A catalyst solution was prepared consisting of 0.0122 g of rhodium dicarbonyl acetylacetonate (250 ppm rhodium), 0.1815 g of (isoBHA-P)$_2$-(−)-2,3-0-isopropylidene-d-threitol prepared in Example 4 (4:1 ligand to rhodium ratio) and 19.8 g of toluene. 15 ml of this solution was charged to a 100 ml reactor and heated under nitrogen to 70° C. 1.5 ml of styrene was charged to the reactor and the reactor pressurized to 130 psi with 1:1 syn gas. The rate of the reaction was determined by monitoring the drop in pressure as syn gas was consumed. Reaction rate was approximately 0.40 g-mole/liter/hour. When the rate had slowed due to consumption of the styrene starting material, the reaction mixture was removed from the reactor under a nitrogen atmosphere.

A portion of the reaction mixture was analyzed by gas chromatography to determine product composition. An isomer ratio of 8.8:1 (2-phenylpropionaldehyde:hydrocinnamaldehyde) was observed.

3 ml of the solution was diluted in 50 ml of acetone and treated with 0.3 g of potassium permanganate and 0.32 g of magnesium sulfate to effect oxidation of the product aldehydes to their respective acids. The mixture was stirred at room temperature for 30 minutes after which time the solvent was removed under reduced pressure. The residue was extracted three times with 50 ml of hot water. The three aqueous solutions were then combined, filtered and washed with 50 ml of chloroform. The aqueous layer was then acidified with HCl to a pH of 2 and extracted with 50 ml of chloroform. The chloroform was removed in vacuo and the resulting residue dissolved in 0.5 ml of toluene. This solution was analyzed by gas chromatography on a chiral b-cyclodextrin column which could separate the two enantiomers of the resulting 2-phenylpropionic acid. This analysis indicated an 52:48 ratio of the S and R enantiomers for an ee (enantiomeric excess) of 2%.

EXAMPLE 32

Asymmetric Hydroformylation of Styrene with bis(diphenylphosphino)-2R,4R-pentanediol/rhodium Catalyst A catalyst solution was prepared consisting of 0.0122 g of rhodium dicarbonyl acetylacetonate (250 ppm rhodium), 0.0917 g of bis(diphenyphosphino)-2R,4R-pentanediol prepared in Example 5 (4:1 ligand to rhodium ratio) and 19.8 g of toluene. 15 ml of this solution was charged to a 100 ml reactor and heated under nitrogen to 70° C. 1.5 ml of styrene was charged to the reactor and the reactor pressurized to 130 psi with 1:1 syn gas. The rate of the reaction was determined by monitoring the drop in pressure as syn gas was consumed. Reaction rate was approximately 0.08 g-mole/liter/hour. When the rate had slowed due to consumption of the styrene starting material, the reaction mixture was removed from the reactor under a nitrogen atmosphere.

A portion of the reaction mixture was analyzed by gas chromatography to determine product composition. An isomer ratio of 3.38:1 (2-phenylpropionaldehyde:hydrocinnamaldehyde) was observed.

3 ml of the solution was diluted in 50 ml of acetone and treated with 0.3 g of potassium permanganate and 0.32 g of magnesium sulfate to effect oxidation of the product aldehydes to their respective acids. The mixture was stirred at room temperature for 30 minutes after which time the solvent was removed under reduced pressure. The residue was extracted three times with 50 ml of hot water. The three aqueous solutions were then combined, filtered and washed with 50 ml of chloroform. The aqueous layer was then acidified with HCl to a pH of 2 and extracted with 50 ml of chloroform. The chloroform was removed in vacuo and the resulting residue dissolved in 0.5 ml of toluene. This solution was analyzed by gas chromatography on a chiral b-cyclodextrin column which could separate the two enantiomers of the resulting 2-phenylpropionic acid. This analysis indicated an 52.5:47.5 ratio of the S and R enantiomers for an ee (enantiomeric excess) of 5%.

EXAMPLE 33

Asymmetric Hydroformylation of Styrene with tris(S-1,1'-bi-2-naphthol) bisphosphite/rhodium Catalyst A catalyst solution was prepared consisting of 0.0122 g of rhodium dicarbonyl acetylacetonate (250 ppm rhodium), 0.1775 g of tris(S-1,1'-bi-2-naphthol) bisphosphite prepared in Example 6 (4:1 ligand to rhodium ratio) and 19.8 g of toluene. 15 ml of this solution was charged to a 100 ml reactor and heated under nitrogen to 70° C. 1.5 ml of styrene was charged to the reactor and the reactor pressurized to 130 psi with 1:1 syn gas. The rate of the reaction was determined by monitoring the drop in pressure as syn gas was consumed. Reaction rate was approximately 0.16 g-mole/liter/hour. When the rate had slowed due to consumption of the styrene starting material, the reaction mixture was removed from the reactor under a nitrogen atmosphere.

A portion of the reaction mixture was analyzed by gas chromatography to determine product composition. An isomer ratio of 2.95:1 (2-phenylpropionaldehyde:hydrocinnamaldehyde) was observed.

3 ml of the solution was diluted in 50 ml acetone and treated with 0.3 g of potassium permanganate and 0.32 g of magnesium sulfate to effect oxidation of the product aldehydes to their respective acids. The mixture was stirred at room temperature for 30 minutes after which time the solvent was removed under reduced pressure. The residue was extracted three times with 50 ml of hot water. The three aqueous solutions were then combined, filtered and washed with 50 ml of chloroform. The aqueous layer was then acidified with HCl to a pH of 2 and extracted with 50 ml of chloroform. The chloroform was removed in vacuo and the resulting residue dissolved in 0.5 ml of toluene. This solution was analyzed by gas chromatography on a chiral b-cyclodextrin column which could separate the two enantiomers of the resulting 2-phenylpropionic acid. This analysis indicated an 62.5:37.5 ratio of the S and R enantiomers for an ee (enantiomeric excess) of 25%.

EXAMPLE 34

Asymmetric Hydroformylation of Styrene with (N,N'-diphenylethylenediamine-P)$_2$-2S,4S-pentanediol/ rhodium Catalyst A catalyst solution was prepared consisting of 0.0127 g of rhodium dicarbonyl acetylacetonate (250 ppm rhodium), 0.0370 g of (N,N'-diphenylethylenediamine-P)$_2$-2S,4S-pentanediol prepared in Example 7 (1:1 ligand to rhodium ratio) and 19.8 g of toluene. 15 ml of this solution was charged to a 100 ml reactor and heated under nitrogen to 70° C. 1.5 ml of styrene was charged to the reactor and the reactor pressurized to 130 psi with 1:1 syn gas. The rate of the reaction was determined by monitoring the drop in pressure as syn gas was consumed. Reaction rate was approximately 0.81 g-mole/liter/hour. When the rate had slowed due to consumption of the styrene starting material, the reaction mixture was removed from the reactor under a nitrogen atmosphere.

A portion of the reaction mixture was analyzed by gas chromatography to determine product composition. An isomer ratio of 7.25:1 (2-phenylpropionaldehyde:hydrocinnamaldehyde) was observed.

A second portion of the reaction mixture was analyzed on a chiraldex B-TA gas chromatography column to determine stereoselectivity. A 53:47 ratio, a 6% ee, was observed with R-2-phenylpropionaldehyde as the major product.

EXAMPLE 35

Asymmetric Hydroformylation of Styrene with (Biphenol-P)$_2$-2S,4S-pentanediol/rhodium Catalyst A catalyst solution was prepared consisting of 0.0125 g of rhodium dicarbonyl acetylacetonate (250 ppm rhodium), 0.0311 g of (biphenol-P)$_2$-2S,4S-pentanediol prepared in Example 8 (1.2:1 ligand to rhodium ratio) and 19.9 g of acetone. 15 ml of this solution was charged to a 100 ml reactor and heated under nitrogen to 70° C. 1.5 ml of styrene was charged to the reactor and the reactor pressurized to 130 psi with 1:1 syn gas. The rate of the reaction was determined by monitoring the drop in pressure as syn gas was consumed. Reaction rate was approximately 0.7 g-mole/liter/hour. When the rate had slowed due to consumption of the styrene starting material, the reaction mixture was removed from the reactor under a nitrogen atmosphere.

A portion of the reaction mixture was analyzed by gas chromatography to determine product composition.

An isomer ratio of 4.6:1 (2-phenylpropionaldehyde:hydrocinnamaldehyde) was observed.

A second portion of the reaction mixture was analyzed on a Chiraldex B-TA gas chromatography column to determine stereoselectivity. A 57:43 ratio, a 14% ee, was observed with R-2-phenylpropionaldehyde as the major product.

EXAMPLE 36

Asymmetric Hydroformylation of Styrene with (isoBHA-P)$_2$-2R,4R-pentanediol/rhodium Catalyst A catalyst solution was prepared consisting of 0,0184 g of rhodium dicarbonyl acetylacetonate (250 ppm rhodium), 0.2556 g of (isoBHA-P)$_2$-2R, 4R-pentanediol prepared in Example 1 (4:1 ligand to rhodium ratio) 5 g of 1-hexene and 24,7 g of acetone. The solution was charged to a 100 ml reactor which was pressurized to 600 psi with 1:1 syn gas, The rate of the reaction was determined by monitoring the drop in pressure as syn gas was consumed. Reaction rate was approximately 0,15g-mole/liter/hour, When the rate had slowed due to consumption of the starting material, the reaction mixture was removed from the reactor under a nitrogen atmosphere, A portion of the reaction mixture was analyzed by gas chromatography to determine product composition. A 2:1 isomer ratio of 2-methylhexanal to n-heptanal was observed, A second portion of the solution was analyzed on a Chiraldex B-TA gas chromotography column to determine enantioselectivity. A 60:40 distribution of enantiomers, a 20% ee, was observed with the S-2-methylhexanal isomer as the major product.

EXAMPLE 37

Asymmetric Hydroformylation of Alpha-Methylstyrene with (isoBHA-P)$_2$-2R,4R-pentanediol/rhodium Catalyst A catalyst solution was prepared consisting of 0.0297 g of rhodium dicarbonyl acetylacetonate (250 ppm rhodium), 0.4074 g of (isoBHA-P)$_2$-2R,4R-pentanediol prepared in Example 1 (4:1 ligand to rhodium ratio), 15 g of alpha-methylstyrene and 14.6 g of acetone. The solution was charged to a 100 ml reactor and heated under nitrogen to 50° C. The reactor was pressurized to 600 psi with 1:1 syn gas. The rate of the reaction was determined by monitoring the drop in pressure as syn gas was consumed. Reaction rate was approximately 0.15 g-mole/liter/hour. The reaction mixture was removed from the reactor under a nitrogen atmosphere.

A portion of the reaction mixture was analyzed by gas chromatography to determine product composition. Only a single regioisomer, 3-phenylbutyraldehyde, was observed.

A second portion of the solution was analyzed on a Chiraldex B-TA gas chromatography column to determine enantioselectivity. A 63:37 distribution of enantiomers, a 26% ee, was observed with S stereoisomer as the major product.

EXAMPLE 38

Asymmetric Hydroformylation of Styrene with (iSoBHA-P)$_2$-2R,4R-pentanediol/ruthenium Catalyst A catalyst solution was prepared consisting of 0.0596 g of ruthenium (III) (acetylacetonate)$_3$(500 ppm ruthenium), 0.2554 g of (isoBHA-P)$_2$-2R,4R-pantanediol prepared in Example 1 (2:1 ligand to ruthenium ratio), 14.5 g of acetone and 15.2 g of styrene. This solution was charged to a 100 ml reactor and heated under nitrogen to 70° C. The reactor was pressurized to 500 psi with 1:1 syn gas. The rate of the reaction was determined by monitoring the drop in pressure as syn gas was consumed. Reaction rate was approximately 0.25 g-mole/liter/hour. When the rate had slowed due to consumption of the styrene starting material, the reaction mixture was removed from the reactor under a nitrogen atmosphere.

A portion of the reaction mixture was analyzed by gas chromatography to determine product composition. An isomer ratio of 17:1 (2-phenylpropionaldehyde:hydrocinnamaldehyde) was observed.

3 ml of the solution was diluted in 50 ml of acetone and treated with 0.3 g of potassium permanganate and 0.32 g of magnesium sulfate to effect oxidation of the product aldehydes to their respective acids. The mixture was stirred at room temperature for 30 minutes after which time the solvent was removed under reduced pressure. The residue was extracted three times with 50 ml of hot water. The three aqueous solutions were then combined, filtered and washed with 50 ml of chloroform. The aqueous layer was then acidified with HCl to a pH of 2 and then extracted with 50 ml of chloroform. The chloroform was removed in vacuo and the resulting residue dissolved in 0.5 ml of toluene. This solution was analyzed by gas chromatography on a chiral b-cyclodextrin column which could separate the two enantiomers of the resulting 2-phenylpropionic acid. This analysis indicated an 77:23 ratio of the S and R enantiomers for an ee (enantiomeric excess) of 54%.

EXAMPLE 39

Asymmetric Hydroformylation of p-isobutylstyrene with (isoBHA-P)$_2$-2R,4R-pentanediol/rhodium Catalyst A catalyst solution was prepared consisting of 0.1097 g rhodium dicarbonyl acetylacetonate (1500 ppm rhodium), 0.7654 g of (isoBHA-P)$_2$-2R,4R-pentanediol prepared as in Example 1 (4:1 ligand to rhodium ratio), 5 g p-isobutylstyrene and 24.5 g acetone. This solution was charged to a 100 ml reactor and charged to a pressure of 67 psi with hydrogen gas and to 200 psi with CO. The rate of the reaction was determined by monitoring the drop in pressure as syn gas was consumed. Reaction rate was approximately 0.1 g-mole/liter/hour. When the rate had slowed due to consumption of the styrene starting material, the reaction mixture was removed from the reactor under a nitrogen atmosphere.

A portion of the reaction mixture was analyzed by gas chromatography to determine product composition. An isomer ratio of 66:1 (2-(4-isobutyl) -phenylpropionaldehyde:3-(4-isobutyl)phenylpropionaldehyde) was observed.

3 ml of the solution was diluted in 50 ml acetone and treated with 0.3 g potassium permanganate and 0.32 g magnesium sulfate to effect oxidation of the product aldehydes to their respective acids. The mixture was stirred at room temperature for 30 minutes after which time the solvent was removed under reduced pressure. The residue was extracted three times with 50 ml of hot water. The three aqueous solutions were then combined, filtered and washed with 50 ml chloroform. The aqueous layer was then acidified with HCl to a pH of two and then extracted with 50 ml of chloroform. The chloroform was removed in vacuo and the resulting residue dissolved in 0.5 ml toluene. This solution was analyzed by gas chromatography on a chiral b-cyclodextrin column which could separate the two enantiomers of the resulting 2-phenylpropionic acid. This analysis indicated an 91:9 ratio of the S and R enantiomers for an ee (enantiomeric excess) of 82%.

EXAMPLE 40

Asymmetric Hydroformylation of Methoxyvinylnaphthalene with (isoBHA-P)$_2$-2R,4R-pentanediol/rhodium Catalyst A catalyst solution was prepared consisting of 0.0366 g rhodium dicarbonyl acetylacetonate (500 ppm rhodium), 0.5103 g of (isoBHA-P)$_2$-2R,4R-pentanediol prepared as in Example 1 (4:1 ligand to rhodium ratio), 5 g methoxyvinylnaphthalene and 24.5 g acetone. This solution was charged to a 100 ml reactor and charged to a pressure of 40 psi with hydrogen gas and 200 psi with CO. The rate of the reaction was determined by monitoring the drop in pressure as syn gas was consumed. Reaction rate was approximately 0.1 g-mole/liter/hour. When the rate had slowed due to consumption of the styrene starting material the reaction mixture was removed from the reactor under a nitrogen atmosphere.

A portion of the reaction mixture was analyzed by gas chromatography to determine product composition. An isomer ratio of 80:1 (2-(6-methoxy)naphthylpropionaldehyde :3-(6-methoxy)naphthylpropionaldehyde) was observed.

3 ml of the solution was diluted in 50 ml acetone and treated with 0.3 g potassium permanganate and 0.32 g magnesium sulfate to effect oxidation of the product aldehydes to their respective acids. The mixture was stirred at room temperature for 30 minutes after which time the solvent was removed under reduced pressure. The residue was extracted three times with 50 ml of hot water. The three aqueous solutions were then combined, filtered and washed with 50 ml chloroform. The aqueous layer was then acidified with HCl to a pH of two and then extracted with 50 ml of chloroform. The chloroform was removed in vacuo and the resulting residue dissolved in 0.5 ml toluene. This solution was analyzed by gas chromatography on a chiral b-cyclodextrin column which could separate the two enantiomers of the resulting 2-phenylpropionic acid. This analysis indicated an 92.5:7.5 ratio of the S and R enantiomers for an ee (enantiomeric excess) of 85%.

EXAMPLE 41

Asymmetric Hydrosilylation of Acetophenone with (isoBHA-P)$_2$-2R,4R-pentanediol/rhodium Catalyst Bis(bicyclo[2.2.1]hepta-2,5-diene)rhodium(I) perchlorate (0.020 g) and 0.200 g of (isoBHA-P)$_2$-2R,4R-pentanediol prepared in Example 1 (4.8:1 ligand to rhodium ratio) were charged to a 50 ml Schlenk flask under nitrogen. Tetrahydrofuran (THF) (5.0 ml) was added to dissolve catalyst. 0.58 ml of acetophenone and 0.93 ml of diphenylsilane were added to the flask via syringe. The solution was stirred under nitrogen for 18 hours. The solution was treated with 10 ml of 10% hydrochloric acid and extracted two times with 10 ml of diethyl ether.

This solution was analyzed by gas chromatography on a Chiraldex B-PH column which could separate the two enantiomers of the resulting sec-phenethyl alcohol. This analysis indicated an 80:20 ratio of the R and S enantiomers for an ee (enantiomeric excess) of 60%.

EXAMPLE 42

Asymmetric Hydrocyanation of Styrene with (isoBHA-P)$_2$-2R,4R-pentanediol/nickel Catalyst Bis(1,5-cyclooctadiene)nickel(0) (0.025 g) and 0.146 g of (isoBHA-P)$_2$-2R,4R-pentanediol prepared in Example 1 (2:1 ligand to nickel ratio) were charged to a 50 ml Schlenk flask under nitrogen. Deoxygenated THF (10 ml) was added, and the solution was stirred for 30 minutes. 2.0 ml of styrene and 2.00 ml of acetone cyanohydrin were added to the flask via syringe. The solution was stirred for 24 hours at 25° C.

A portion of this solution was analyzed by gas chromatography to determine product composition. An isomer ratio of 2:1 (α-methylbenzyl cyanide: hydrocinnamonitrile) was observed. A second portion of this solution was analyzed by gas chromatography on a Chiraldex G-TA column which could separate the two enantiomers of the resulting α-methylbenzyl cyanide. Only a single regioisomer of 2-norbornane carbonitrile was observed by this analysis. This analysis indicated an 82:18 ratio of the enantiomers for an ee (enantiomeric excess) of 64%.

EXAMPLE 43

Asymmetric Hydrocyanation of Norbornene with (isoBHA-P)$_2$-2R,4R-pentanediol/nickel Catalyst Bis(1,5-cyclooctadiene)nickel(0) (0.021 g) and 0.046 g of (isoBHA-P)$_2$-2R,4R-pentanediol prepared in Example 1 (1:1 ligand to nickel ratio) were charged to a 50 ml Schlenk flask under nitrogen. Deoxygenated THF (5.0 ml) was added, and the solution was stirred under nitrogen for 30 minutes. 0.500 g of norbornene and 1.00 ml of acetone cyanohydrin were added to the flask via syringe. The solution was refluxed under nitrogen for 5 hours.

This reaction mixture was analyzed by gas chromatography on a Chiraldex B-PH column which could separate the two enantiomers of the resulting 2-norbornane carbonitrile. Only a single regioisomer of 2-norbornane carbonitrile was observed by this analysis. This analysis indicated an 75:25 ratio of the enantiomers for an ee (enantiomeric excess) of 50%.

EXAMPLE 44

Asymmetric Hydrocyanation of Styrene with tris(S-1,1'-bi-2-naphthol) bisphosphite/nickel Catalyst Bis(1,5-cyclooctadiene)nickel(0) (0.030 g) and 0.173 g of tris(S-1,1'-bi-2-naphthol) bisphosphite prepared in Example 6 (2:1 ligand to nickel ratio) were charged to a 50 ml Schlenk flask under nitrogen. Deoxygenated THF (10 ml) was added, and the solution was stirred for 30 minutes. 2.0 ml of styrene and 2.00 ml of acetone cyanohydrin were added to the flask via syringe. The solution was stirred for 24 hours at 25° C.

A portion of this solution was analyzed by gas chromatography to determine product composition. An isomer ratio of 220:1 (α-methylbenzyl cyanide: hydrocinnamonitrile) was observed. A second portion of this solution was analyzed by gas chromatography on a Chiraldex G-TA column which could separate the two enantiomers of the resulting α-methylbenzyl cyanide. Only a single regioisomer of 2-norbornane carbonitrile was observed by this analysis. This analysis indicated an 56.5:43.5 ratio of the enantiomers for an ee (enantiomeric excess) of 13%.

EXAMPLE 45

Asymmetric Transfer Hydrogenation of Acetophenone with (isoBHA-P)$_2$-2R,4R-pentanediol/iridium Catalyst Bicyclo[2.2.1]hepta-2,5-diene iridium(I)chloride dimer (0.015 g) and 0.200 g of (isoBHA-P)$_2$-2R,4R-pentanediol prepared in Example 1 (5:1 ligand to iridium ratio) were charged to a 50 ml Schlenk flask under nitrogen. THF (5.0 ml) was added to dissolve the catalyst. To this solution were added 5.0 ml of 2-propanol, 0.58 ml of acetophenone and 0.012 g of potassium hydroxide. The solution was stirred under nitrogen for 24 hours.

This reaction mixture was analyzed by gas chromatography on a Chiraldex B-PH column which could separate the two enantiomers of the resulting sec-phenethyl alcohol. This analysis indicated an 60:40 ratio of the S and R enantiomers for an ee (enantiomeric excess) of 20%.

EXAMPLE 46

Asymmetric Hydrogenation of Itaconic Acid with tris(S-1,1'-bi-2-naphthol) bisphosphite/rhodium Catalyst A catalyst solution was prepared consisting of 0.040g bis(bicyclo[2.2.1]hepta-2,5-diene)rhodium(I) hexafluorophosphate, 0.100 g of tris(S-1,1'-bi-2-naphthol) bisphosphite prepared in Example 6 (1.7:1 ligand to rhodium ratio) and 10 ml of tetrahydrofuran. The solution was charged to a 100 ml reactor and heated to 35° C. The reactor was pressurized to 1000 psi with hydrogen and stirred for 15 minutes. The reactor was vented, and a solution of 0.50 g of itaconic acid and 5 ml of tetrahydrofuran was added to the reactor. The reactor was pressurized with 1000 psi of hydrogen and stirred for 2 hours.

A portion of the reaction mixture was analyzed by gas chromatography on a Chiraldex B-PH column which could separate the two enantiomers of the resulting alpha-methyl succinic acid. This analysis indicated an 60:40 ratio of the enantiomers for an ee (enantiomeric excess) of 20%.

EXAMPLE 47

Asymmetric Hydroboration of Styrene with (isoBHA-P)$_2$-2R,4R-pentanediol/rhodium Catalyst Bis(bicyclo[2.2.1]hepta-2,5-diene)rhodium(I) hexafluorophosphate (0.010 g) and 0.050 g of (isoBHA-P)$_2$-2R,4R-pentanediol prepared in Example 1 (2.7:1 ligand to rhodium ratio) were charged to a 50 ml Schlenk flask under nitrogen. Distilled 1,2-dimethoxyethane (2.0 ml) was added to the flask. 0.23 ml of styrene and 0.23 ml of catecholborane were added to the flask via syringe. The solution was stirred under nitrogen for 2 hours. The solution was treated with 4 ml of methanol, 4.8 ml of 3.0 mol/liter sodium hydroxide solution and 0.52 ml of 30% hydrogen peroxide. The solution was stirred for 3 hours and extracted with 10 ml of diethyl ether.

A portion of this solution was analyzed by gas chromatography to determine product composition. An isomer ratio of 3:1 (sec-phenethyl alcohol:2-phenylethanol) was observed. A second portion of this solution was analyzed by gas chromatography on a Chiraldex B-PH column which could separate the two enantiomers of the resulting sec-phenethyl alcohol. This analysis indicated an 61:39 ratio of the S and R enantiomers for an ee (enantiomeric excess) of 22%.

EXAMPLE 48

Asymmetric Cyclopropanation of Styrene with (isoBHA-P)-S-1,1'-bi-2-naphthol diorganophosphite/copper Catalyst Copper(I) chloride (0.010 g) and 0.085 g of isoBHA-P-S-1,1'-bi-2-naphthol diorganophosphite prepared in Example 9 (1.2:1 ligand to copper ratio) were charged to a 25 ml Schlenk flask under nitrogen. Toluene (5.0 ml) was added to the flask under nitrogen. 0.10 ml of triethylamine was added to the flask via syringe, and the solution was stirred under nitrogen for 15 minutes. 5.0 ml of styrene was added by syringe followed by 0.250 ml of ethyldiazoacetate. The solution was stirred under nitrogen for 2 hours.

A portion of the reaction mixture was analyzed by gas chromatography to determine product composition. An isomer ratio of 2.1:1 (trans:cis) was observed for the product cyclopropanes. A second portion of this solution was analyzed by gas chromatography on a Chiraldex B-PH column which could separate the two enantiomers of the resulting cis-ethyl-2-phenylcyclopropanecarboxylate. This analysis indicated an 63:37 ratio of the cis cyclopropane enantiomers for an ee (enantiomeric excess) of 26%.

EXAMPLE 49

Asymmetric Hydrosilylation of Styrene with (S-1,1'-bi-2-naphthol-P)-2,6-di-t-butyl-4-methylphenol diorganophosphite/palladium Catalyst Cis-dichlorobis(acetonitrile)palladium(II) (0.015 g) and 0.050 g of S-1,1'-bi-2-naphthol-P-2, 6-di-t-butyl-4-methylphenol diorganophosphite prepared in Example 10 (1.6:1 ligand to palladium ratio) were charged to a 50 ml Schlenk flask under nitrogen. Toluene (5.0 ml) was added to the flask. 0.55 ml of styrene and 0.55 ml of trichlorosilane were added to the solution via syringe, and the solution was stirred under nitrogen for 24 hours.

A portion of the reaction mixture was analyzed by gas chromatography to determine the product composition. Only a single regioisomer, 2-trichlorosilylethylbenzene, was observed.

The reaction mixture was concentrated to an oil under vacuum and dissolved in 5.0 ml of absolute ethanol. 1.0 ml of triethylamine was added to the solution. This solution was analyzed by gas chromatography on a Chiraldex B-PH column which could separate the two enantiomers of the resulting 2-triethoxysilylethylbenzene. This analysis indicated an 58:42 ratio of the enantiomers for an ee (enantiomeric excess) of 16%.

EXAMPLE 50

Asymmetric Aldol Condensation of Benzaldehyde and Methyl trimethylsilyl dimethylketene acetal with (isoBHA-P)$_2$-2R,4R-pentanediol/rhodium Catalyst Bis(bicyclo[2.2.1]hepta-2,5-diene)rhodium(I) hexafluorophosphate (0.012 g) and 0.050 g of (isoBHA-P)$_2$-2R,4R-pentanediol prepared in Example 1 (2.2:1 ligand to rhodium ratio) were charged to a 50 ml Schlenk flask under nitrogen. Dichloromethane (2.0 ml) was added to the flask under nitrogen. 0.20 ml of benzaldehyde and 0.40 ml of methyl trimethylsilyl dimethylketene acetal were added to the flask via syringe. The solution was stirred under nitrogen for 18 hours. The solution was treated with 10 ml of 10% hydrochloric acid and extracted two times with 10 ml of diethyl ether.

This solution was analyzed by gas chromatography on a Chiraldex B-PH column which could separate the two enantiomers of the resulting methyl-2,2-dimethyl-3-phenyl-3-trimethylsiloxypropionate. This analysis indicated an 53:47 ratio of the enantiomers for an ee (enantiomeric excess) of 6%.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A hydrogenation process which comprises reacting a prochiral compound (which is a compound having the potential to be converted to a chiral product in the hydrogenation process) or chiral compound (which is a compound which has one or more centers of asymmetry) in the presence of an optically active metal-ligand complex catalyst to produce an optically active product (which is a mixture of stereoisomers which rotates the plane polarized light due to an excess of one of the steroisomers over the others), said optically metal-ligand complex catalyst comprising a metal complexed with an optically active ligand having the formula

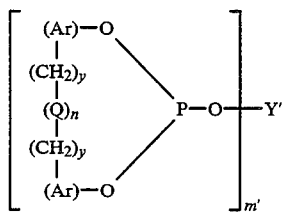

wherein each Ar group is the same or different and is a substituted or unsubstituted aryl radical; Y is an m-valent substituted or unsubstituted hydrocarbon radical selected form alkylene, alkylene-oxy-alkylene, arylene, and arylene-$(CH_2)_y$—$(Q)_n$—$(CH_2)_y$-arylene; each Ar contains from 6 to 18 carbon atoms Y' contains from 2 to 30 carbon atoms; each y is the same or different and is a value of 0 to 1; each n is the same or different and is a value of 0 or 1; each Q is the same or different and is a substituted or unsubstituted divalent bridging group selected from —$C^1R^2$, —O—, —S—, —$NR^3$—, $SiR^4R^5$—, and —CO—, wherein $R^1$ and $R^2$ are the same or different and are hydrogen or a substituted or unsubstituted radical selected from alkyl or 1 to 12 carbon atoms, phenyl, tolyl and anisyl, and $R^3$, $R^4$ and $R^5$ are the same or different and are a radical selected from hydrogen or methyl; and m is a value of from 2 to 6.

2. The process of claim 1 is which the optically active metal-ligand complex catalyst comprises a metal selected from a Group VIII, Group IB and Group VIB metal complexed with said optically active ligand.

3. The process of claim 1 in which the optically active metal-ligand complex catalyst comprises a Group VIII metal-polyphosphite complex catalyst.

4. The process of claim 1 in which the optically active metal-ligand complex catalyst comprises a Group VIII metal-diorganophosphite complex catalyst.

5. The process of claim 1 in which the optically active metal-ligand catalyst comprises a Group VIII metal-bisphosphite complex catalyst.

6. The process of claim 2 in which the Group VIII metal comprises rhodium or ruthenium.

7. The process of claim 1 which is carried out in the added presence of free ligand.

8. The process of claim 1 in which the optically active metal-ligand complex catalyst is selected from a rhodium-(poly)phosphite complex catalyst, a rhodium-(poly)phosphinite complex catalyst and a rhodium-(poly)phosphonite complex catalyst.

9. The process of claim 1 in which the prochiral or chiral compound comprises a substituted or unsubstituted olefin.

10. The process of claim 1 in which the optically active product comprises a substituted or unsubstituted aldehyde, ketone, carboxylic acid, amide, ester, alcohol, amine or ether.

11. An optically active produce produced by the process of claim 1.

12. The process of claim 2 in which the Group VIII metal is selected from rhodium, cobalt, iridium, ruthenium, iron, nickel, palladium, platinum, osmium and mixtures thereof.

* * * * *